US012620223B2

(12) United States Patent
Addis et al.

(10) Patent No.: US 12,620,223 B2
(45) Date of Patent: May 5, 2026

(54) IDENTIFYING VARIATION IN SURGICAL APPROACHES

(71) Applicant: DIGITAL SURGERY LIMITED, London (GB)

(72) Inventors: Carole RJ Addis, London (GB); Sheldon K. Hall, London (GB); Pinja ME Haikka, Hove (GB); George Bruce Murgatroyd, Hitchin (GB)

(73) Assignee: DIGITAL SURGERY LIMITED, London (GB)

( * ) Notice: Subject to any disclaimer, the term of this patent is extended or adjusted under 35 U.S.C. 154(b) by 180 days.

(21) Appl. No.: 18/281,995

(22) PCT Filed: Apr. 14, 2022

(86) PCT No.: PCT/EP2022/060030
§ 371 (c)(1),
(2) Date: Sep. 14, 2023

(87) PCT Pub. No.: WO2022/219126
PCT Pub. Date: Oct. 20, 2022

(65) Prior Publication Data
US 2024/0153269 A1 May 9, 2024

Related U.S. Application Data

(60) Provisional application No. 63/208,171, filed on Jun. 8, 2021, provisional application No. 63/175,209, filed on Apr. 15, 2021.

(51) Int. Cl.
*G06V 20/40* (2022.01)
*G06T 11/20* (2006.01)
(Continued)

(52) U.S. Cl.
CPC ............ *G06V 20/41* (2022.01); *G06T 11/206* (2013.01); *G06V 10/761* (2022.01);
(Continued)

(58) Field of Classification Search
CPC ...... G06F 16/287; G06F 16/34; G06F 16/358; G06T 11/206; G06T 2200/24;
(Continued)

(56) References Cited

U.S. PATENT DOCUMENTS

| | | | |
|---|---|---|---|
| 10,147,052 | B1 | 12/2018 | Lendvay et al. |
| 10,607,158 | B2 | 3/2020 | Lendvay et al. |

(Continued)

OTHER PUBLICATIONS

Krishnan et al., Transition state clustering: Unsupervised surgical trajectory segmentation for robot learning. 2017, The International Journal of Robotics, SageJournals, vol. 36, Issue 13-14, pp. 1-24 https://doi.org/10.1177/0278364917743319 (Year: 2017).*

(Continued)

*Primary Examiner* — Said Broome
(74) *Attorney, Agent, or Firm* — CANTOR COLBURN LLP; Robert Crist

(57) ABSTRACT

An aspect includes a computer-implemented method that identifies variations in surgical approaches to medical procedures. Surgical videos documenting multiple cases of a medical procedure are analyzed to identify different surgical approaches used by service providers when performing the medical procedure. According to some aspects surgical phases are identified in each surgical video and groups of similar surgical phase sequences are grouped into surgical approaches.

18 Claims, 17 Drawing Sheets

(51) Int. Cl.

| | |
|---|---|
| *G06V 10/74* | (2022.01) |
| *G06V 10/762* | (2022.01) |
| *G06V 20/70* | (2022.01) |
| *G16H 20/40* | (2018.01) |
| *G16H 50/70* | (2018.01) |
| *G16H 70/20* | (2018.01) |

(52) U.S. Cl.
CPC ............ *G06V 10/762* (2022.01); *G06V 20/49* (2022.01); *G06V 20/70* (2022.01); *G16H 20/40* (2018.01); *G16H 50/70* (2018.01); *G16H 70/20* (2018.01); *G06T 2200/24* (2013.01); *G06V 2201/03* (2022.01)

(58) Field of Classification Search
CPC .... G06V 10/761; G06V 10/762; G06V 20/41; G06V 20/49; G06V 20/70; G06V 2201/03; G16B 45/00; G16B 20/40; G16B 50/70; G16B 70/20
See application file for complete search history.

(56) References Cited

U.S. PATENT DOCUMENTS

| | | | | |
|---|---|---|---|---|
| 11,205,508 | B2 * | 12/2021 | Venkataraman | ....... G06N 20/00 |
| 2015/0044654 | A1 | 2/2015 | Lendvay et al. | |
| 2017/0116873 | A1 | 4/2017 | Lendvay et al. | |
| 2019/0362834 | A1 | 11/2019 | Venkataraman et al. | |
| 2024/0161934 | A1 | 5/2024 | Johnston et al. | |

OTHER PUBLICATIONS

Cheng et al., Dual clustering for categorization of action sequences, 2008 19th International Conference on Pattern Recognition, IEEE, pp. 1-4 https://doi.ieeecomputersociety.org/10.1109/ICPR.2008. 4761247 (Year: 2008).*

Carley et al., "Machine Learning for Surgical Phase Recognition: A Systematic Review", Annals of Surgery, vol. 273, No. 4, Nov. 16, 2020, pp. 684-693.

Ferreira et al., "Approaching Process Mining with Sequence Clustering: Experiments and Findings", Business Process Management, Sep. 2007, 16 pages.

Forestier et al., "Non-Linear Temporal Scaling of Surgical Processes", HAL Open Science, Sep. 2018, 13 pages.

International Search Report and Written Opinion for Application No. PCT/EP2022/060030, International Filing Date: Apr. 14, 2022; Date of Mailing: Jul. 12, 2022; 17 pages.

International Search Report and Written Opinion for Application No. PCT/EP2022/060032, International Filing Date: Apr. 14, 2022; Date of Mailing: Jul. 12, 2022; 17 pages.

Neumuth et al, "Similarity metrics for surgical process models", Artificial Intelligence in Medicine, Oct. 4, 2011, 13 pages.

* cited by examiner

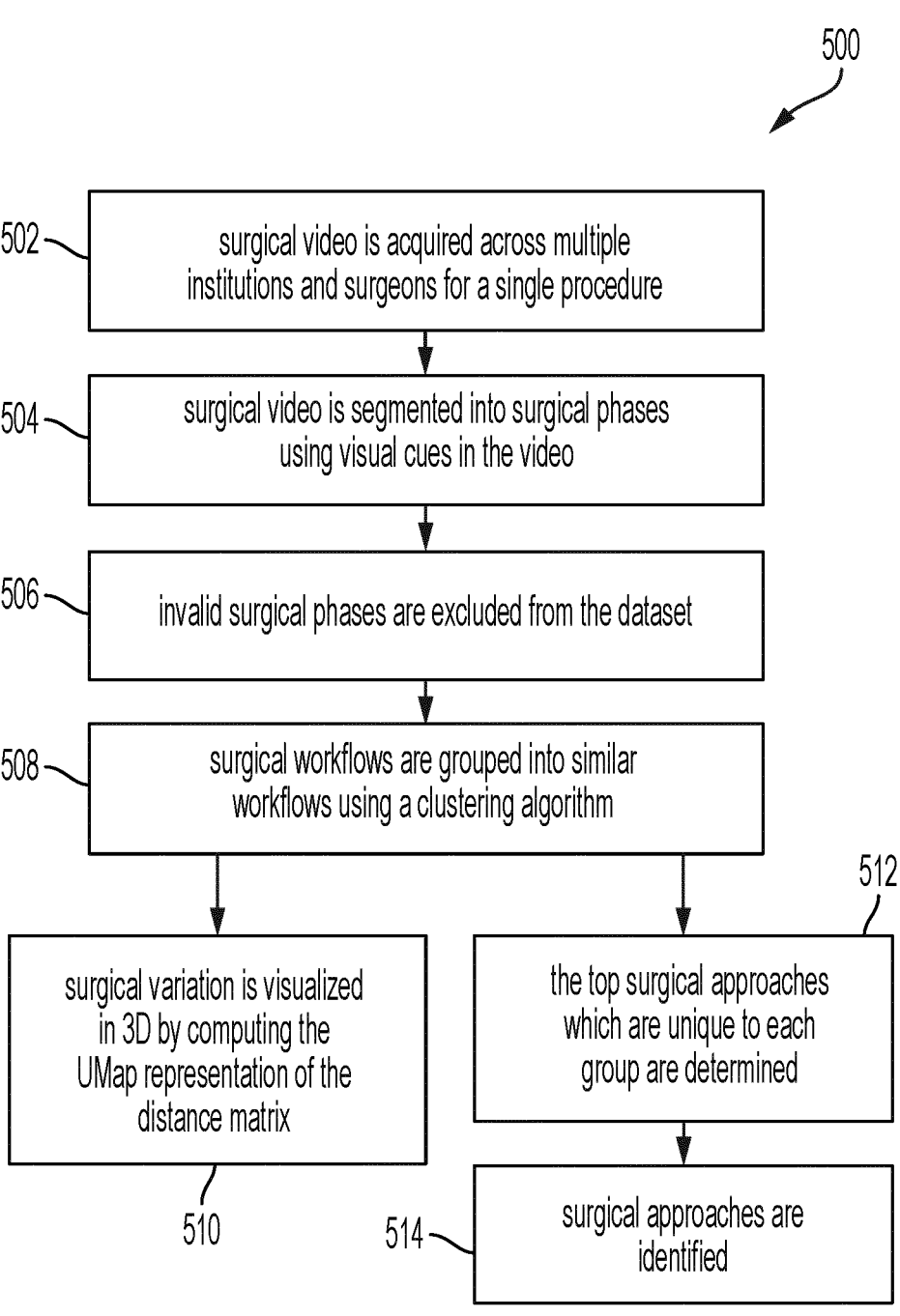

500

502 — surgical video is acquired across multiple institutions and surgeons for a single procedure 504 — surgical video is segmented into surgical phases using visual cues in the video 506 — invalid surgical phases are excluded from the dataset 508 — surgical workflows are grouped into similar workflows using a clustering algorithm 510 — surgical variation is visualized in 3D by computing the UMap representation of the distance matrix 512 — the top surgical approaches which are unique to each group are determined 514 — surgical approaches are identified

602 — distance metric between all pairs of surgical workflows is calculated and stored in a distance matrix 604 — spectral clustering is used to group similar workflows using the distance matrix 606 — optimal clustering hyperparameters are determined

700

SUBSTRING IDENTIFICATION — 702

SUBSEQUENCE IDENTIFICATION — 704

1300 k = 4

● 1
● 2
○ 3
● 4

| Cluster | 1 | 2 | 3 | 4 |
|---|---|---|---|---|
| Cluster size | 125 | 68 | 134 | 39 |
| Num. unique workflows | 48 | 34 | 50 | 16 |
| Num. closed FSPs | 161 | 25 | 58 | 20 |
| Num. unique FSPs | 87 | 16 | 13 | 3 |
| Num. maximal unique FSPs | 5 | 5 | 4 | 1 |

1600

1700

Angle of His Dissection

Biliopancreatic Limb Measurement

Closure of Mesenteric Defects

Create the Roux and BP Limbs

Creation of Gastro-Jejunostomy

Creation of Jejuno-jejunostomy

Creation of Mesocolic Window

Gastric Pouch Creation

Leak Test

Omental Division

Port Insertion

Port Removal and Closure

Retrieve Roux Limb

IDENTIFYING VARIATION IN SURGICAL APPROACHES

CROSS REFERENCE TO RELATED APPLICATIONS

This application is a National Stage application of PCT/EP2022/060030, filed Apr. 14, 2022, which claims the benefit of U.S. Provisional Patent Application No. 63/175,209, filed Apr. 15, 2021 and U.S. Provisional Patent Application No. 63/208, 171, filed Jun. 8, 2021, all of which are incorporated by reference in their entirety herein.

BACKGROUND

The present invention relates in general to computing technology and relates more particularly to computing technology for identifying variations in surgical approaches.

Computer-assisted systems, particularly computer-assisted surgery systems (CASs), rely on video data digitally captured during a surgery. Such video data can be stored and/or streamed. In some cases, the video data can be used to augment a person's physical sensing, perception, and reaction capabilities. For example, such systems can effectively provide the information corresponding to an expanded field of vision, both temporal and spatial, that enables a person to adjust current and future actions based on the part of an environment not included in his or her physical field of view. Alternatively, or in addition, the video data can be stored and/or transmitted for several purposes such as archival, training, post-surgery analysis, and/or patient consultation. The process of analyzing and comparing a large amount of video data from multiple surgical procedures to identify commonalities can be highly subjective and error-prone due, for example, to the volume of data and the numerous factors (e.g., patient condition, physician preferences, etc.) that impact the workflow of each individual surgical procedure that is being analyzed.

SUMMARY

According to one or more aspects, a system includes a machine learning training system that includes one or more machine learning models that are trained to identify a plurality of surgical phases in a video of a surgical procedure. The system also includes a data analysis system configured to identify different surgical approaches in a plurality of videos capturing a same type of surgical procedure. Identifying the different surgical approaches includes receiving a plurality of surgical videos, each of the plurality of surgical videos capturing a workflow of the same type of surgical procedure, segmenting each of the plurality of surgical videos into a plurality of surgical phases based on surgical phases identified by the machine learning training system, and representing each segment in each of the plurality of surgical videos as a symbol. The symbolic representations of the plurality of surgical videos are clustered to form groups of surgical videos having similar workflows and the groups are output to a display device for display. Each group represents a different surgical approach.

In one or more aspects, the identifying different surgical approaches further includes outputting an indication of a surgical service provider associated with one or more of the surgical videos or groups to the display device for display.

In one or more aspects, the surgical service provider is a hospital.

In one or more aspects, the surgical service provider is a physician.

In one or more aspects, the identifying different surgical approaches further includes outputting a comparison of surgical approaches taken by different surgical service providers to the display device for display.

In one or more aspects, the clustering includes calculating a distance metric between each pair of the plurality of surgical videos, storing the calculated distance metrics in a distance matrix, and grouping similar workflows based at least in part on the distance matrix In one or more aspects, the identifying different surgical approaches further includes adding a label to each of the different surgical approaches and outputting the labels to the display device.

According to one or more aspects, a computer-implemented method includes receiving, by a processor, a plurality of surgical videos, each of the plurality of surgical videos capturing a workflow of a same type of surgical procedure and each of the plurality of surgical videos segmented into surgical phases. The method further includes grouping, by the processor, the plurality of surgical videos into groups of similar workflows, the grouping based at least in part on the surgical phases of each of the surgical video. The method further includes identifying, by the processor, surgical approaches that are unique to each of the groups, the identifying based at least in part on the surgical phases of each of the surgical videos.

In one or more aspects, the method further includes labeling each of the unique surgical approaches.

In one or more aspects, the grouping includes applying clustering techniques

In one or more aspects, the applying clustering techniques includes calculating a distance metric between each pair of the plurality of surgical videos, storing the calculated distance metrics in a distance matrix, and grouping similar workflows based at least in part on the distance matrix.

In one or more aspects, the method further includes determining optimal clustering hyperparameters for the plurality of surgical videos In one or more aspects, the method further includes outputting, by the processor to a display device, a graphical representation of the workflows in the groups of similar workflows and the identified surgical approaches.

In one or more aspects, the graphical representation identifies a surgical service provider associated with each of the workflows.

According to one or more aspects, a computer program product includes a memory device having computer-executable instructions stored thereon, which when executed by one or more processors cause the one or more processors to perform operations. The operations include visualizing different surgical approaches used by service providers when performing a surgical procedure. The visualizing includes receiving a plurality of surgical videos, each of the plurality of surgical videos capturing a workflow of a service provider performing the surgical procedure. The visualizing further includes clustering the plurality of surgical videos into clusters of similar workflows and identifying surgical approaches that are unique to each of the clusters. A graphical representation of the identified surgical approaches is output to a display device.

In one or more aspects, visualizing further includes receiving user input via a user interface of the graphical representation, and in response to the user input, outputting to the display device, a second graphical representation that includes a label describing each of the identified surgical approaches.

In one or more aspects, the visualizing further includes receiving user input via a user interface of the graphical representation, and in response to the user input, outputting to the display device, a second graphical representation that includes additional information describing characteristics of one or both of a service provider or a patient.

In one or more aspects, each of the plurality of surgical videos are each segmented into surgical phases and the clustering is based at least in part of the surgical phases In one or more aspects, the clustering includes calculating a distance metric between each pair of the plurality of surgical videos, storing the calculated distance metrics in a distance matrix, and grouping similar workflows based at least in part on the distance matrix Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

FIG. 5 depicts a flowchart of a method for identifying variations in surgical approaches according to one or more aspects;

Figure 1:
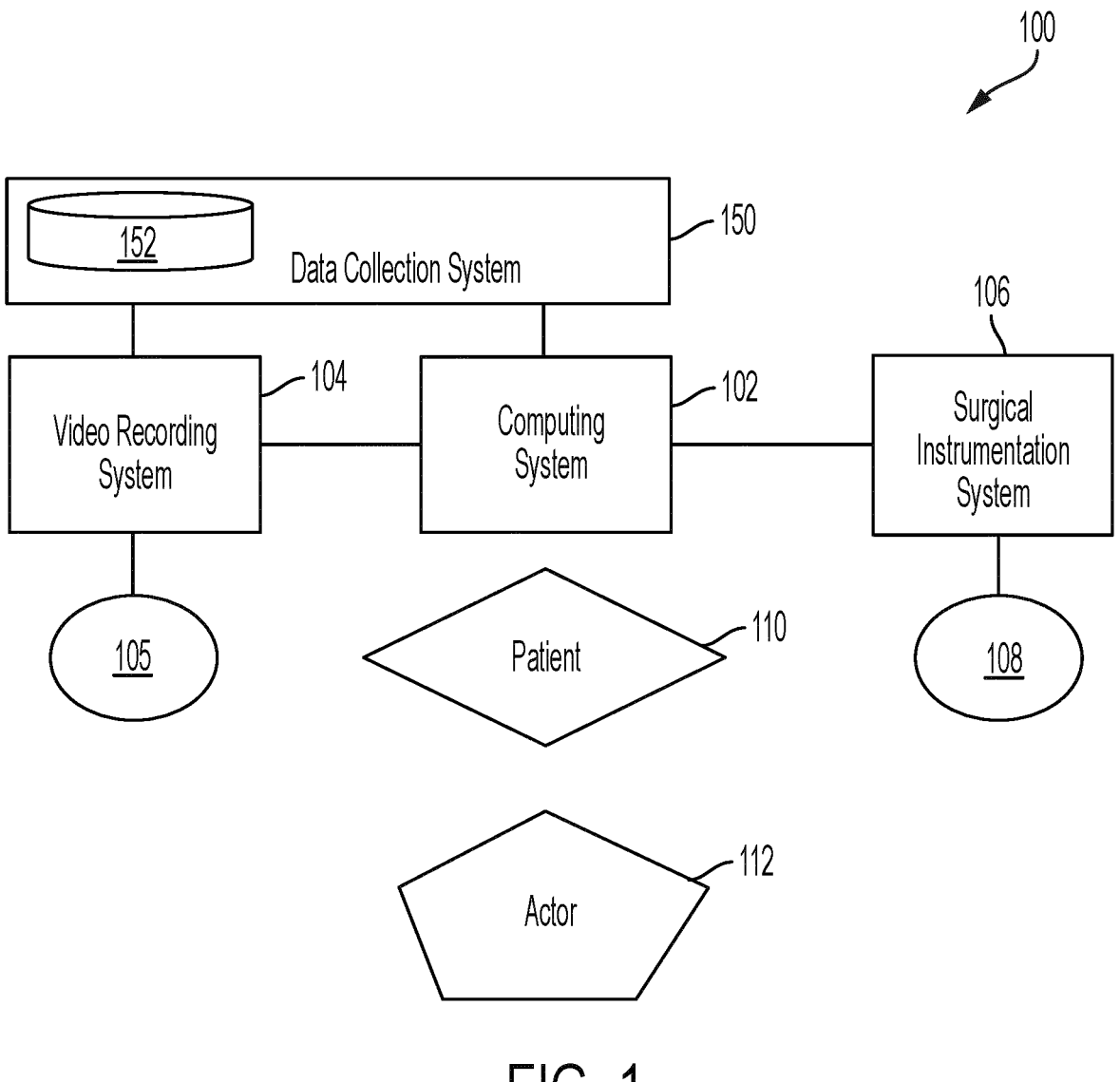
FIG. 1 depicts a computer-assisted surgery (CAS) system according to one or more aspects.

The diagrams depicted herein are illustrative. There can be many variations to the diagrams and/or the operations described herein without departing from the spirit of the invention. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

Exemplary aspects of the technical solutions described herein include systems and methods for identifying variation in surgical approaches to medical procedures. According to aspects, surgical video data of multiple iterations, or cases, of the medical procedure being analyzed are each segmented into phases, and cluster analysis is used to identify different surgical approaches used by service providers when performing the medical procedure. A building block in the effort to standardize surgery is the existence of metrics that can meaningfully capture surgical variability. Being able to identify key surgical approaches within a set of cases can pave the way to correlating different techniques with patient outcomes and efficiency. In order to objectively provide feedback to surgical service providers, such as, but not limited to hospitals, hospital departments, medical practices, and/or surgeons, technical solutions described herein provide a methodology to identify the different approaches that are taken by the different providers. Pattern recognition techniques can be used to identify unique surgical approaches associated with each surgical service provider. Technical solutions described herein facilitate the use of quantitative measures of surgical performance to standardize variable surgical practices, which can be used to improve patient safety and surgical outcomes, and to lower costs.

In exemplary aspects of the technical solutions described herein, surgical data that is captured by a computer-assisted surgical (CAS) system and segmented into surgical phases is input to the analysis described herein to identify different surgical approaches to a medical procedure.

Aspects of the technical solutions described herein allow an analysis of a dataset having a large number of surgical cases (e.g., hundreds or thousands) and a large number of unique surgical phase sequences (e.g., over one hundred). One or more aspects described herein identify groups (or clusters) of similar workflows and determine the unique surgical approaches found within each group. Aspects of the analysis of the technical solutions described herein can reduce the number of unique surgical phase sequences by grouping any sequence data related to surgery. For example, similar phase sequences or step sequences or actions can be grouped into surgical approaches. According to aspects, surgical approaches can include phase substrings (consecutive phases) and subsequences (nonconsecutive phases) found within a set of phase sequences.

Turning now to FIG. 1, an example CAS system 100 is generally shown in accordance with one or more aspects.

The CAS system 100 includes at least a computing system 102, a video recording system 104, and a surgical instrumentation system 106. As illustrated in FIG. 1, an actor 112 can be medical personnel that uses the CAS system 100 to perform a surgical procedure on a patient 110. Medical personnel can be a surgeon, assistant, nurse, administrator, or any other actor that interacts with the CAS system 100 in a surgical environment. The surgical procedure can be any type of surgery, such as but not limited to cataract surgery, laparoscopic cholecystectomy, endoscopic endonasal transsphenoidal approach (eTSA) to resection of pituitary adenomas, or any other surgical procedure. In other examples, actor 112 can be a technician, an administrator, an engineer, or any other such personnel that interacts with the CAS system 100. For example, actor 112 can record data from the CAS system 100, configure/update one or more attributes of the CAS system 100, review past performance of the CAS system 100, repair the CAS system 100, etc.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 108 (e.g., forceps) are used to achieve a specific objective by performing one or more surgical actions.

The video recording system 104 includes one or more cameras 105, such as operating room cameras, endoscopic cameras, etc. The cameras 105 capture video data of the surgical procedure being performed. The video recording system 104 includes one or more video capture devices that can include cameras 105 placed in the surgical room to capture events surrounding (i.e., outside) the patient being operated upon. The video recording system 104 further includes cameras 105 that are passed inside (e.g., endoscopic cameras) the patient 110 to capture endoscopic data. The endoscopic data provides video and images of the surgical procedure.

The computing system 102 includes one or more memory devices, one or more processors, a user interface device, among other components. All or a portion of the computing system 102 shown in FIG. 1 can be implemented for example, by all or a portion of computer system 1000 of FIG. 10. Computing system 102 can execute one or more computer-executable instructions. The execution of the instructions facilitates the computing system 102 to perform one or more methods, including those described herein. The computing system 102 can communicate with other computing systems via a wired and/or a wireless network. In one or more examples, the computing system 102 includes one or more trained machine learning models that can detect and/or predict features of/from the surgical procedure that is being performed or has been performed earlier. Features can include structures such as anatomical structures, surgical instruments 108 in the captured video of the surgical procedure. Features can further include events such as phases, actions in the surgical procedure. Features that are detected can further include the actor 112 and/or patient 110. Based on the detection, the computing system 102, in one or more examples, can provide recommendations for subsequent actions to be taken by the actor 112. Alternatively, or in addition, the computing system 102 can provide one or more reports based on the detections. The detections by the machine learning models can be performed in an autonomous or semi-autonomous manner.

The machine learning models can include artificial neural networks, such as deep neural networks, convolutional neural networks, recurrent neural networks, encoders, decoders, or any other type of machine learning model. The machine learning models can be trained in a supervised, unsupervised, or hybrid manner. The machine learning models can be trained to perform detection and/or prediction using one or more types of data acquired by the CAS system 100. For example, the machine learning models can use the video data captured via the video recording system 104. Alternatively, or in addition, the machine learning models use the surgical instrumentation data from the surgical instrumentation system 106. In yet other examples, the machine learning models use a combination of video data and surgical instrumentation data.

Additionally, in some examples, the machine learning models can also use audio data captured during the surgical procedure. The audio data can include sounds emitted by the surgical instrumentation system 106 while activating one or more surgical instruments 108. Alternatively, or in addition, the audio data can include voice commands, snippets, or dialog from one or more actors 112. The audio data can further include sounds made by the surgical instruments 108 during their use.

In one or more examples, the machine learning models can detect surgical actions, surgical phases, anatomical structures, surgical instruments, and various other features from the data associated with a surgical procedure. The detection can be performed in real-time in some examples. Alternatively, or in addition, the computing system 102 analyzes the surgical data, i.e., the various types of data captured during the surgical procedure, in an offline manner (e.g., post-surgery). In one or more examples, the machine learning models detect surgical phases based on detecting some of the features such as the anatomical structure, surgical instruments, etc.

A data collection system 150 can be employed to store the surgical data, including the video(s) captured during the surgical procedures. The data collection system 150 includes one or more storage devices 152. The data collection system 150 can be a local storage system, a cloud-based storage system, or a combination thereof. Further, the data collection system 150 can use any type of cloud-based storage architecture, for example, public cloud, private cloud, hybrid cloud, etc. In some examples, the data collection system can use a distributed storage, i.e., the storage devices 152 are located at different geographic locations. The storage devices 152 can include any type of electronic data storage media used for recording machine-readable data, such as semiconductor-based, magnetic-based, optical-based storage media, or a combination thereof. For example, the data storage media can include flash-based solid-state drives (SSDs), magnetic-based hard disk drives, magnetic tape, optical discs, etc.

In one or more examples, the data collection system 150 can be part of the video recording system 104, or vice-versa. In some examples, the data collection system 150, the video recording system 104, and the computing system 102, can communicate with each other via a communication network, which can be wired, wireless, or a combination thereof. The communication between the systems can include the transfer of data (e.g., video data, instrumentation data, etc.), data manipulation commands (e.g., browse, copy, paste, move, delete, create, compress, etc.), data manipulation results, etc. In one or more examples, the computing system 102 can manipulate the data already stored/being stored in the data collection system 150 based on outputs from the one or more machine learning models, e.g., phase detection, structure detection, etc. Alternatively, or in addition, the computing system 102 can manipulate the data already stored/being stored in the data collection system 150 based on information from the surgical instrumentation system 106.

In one or more examples, the video captured by the video recording system 104 is stored on the data collection system 150. In some examples, the computing system 102 curates parts of the video data being stored on the data collection system 150. In some examples, the computing system 102 filters the video captured by the video recording system 104 before it is stored on the data collection system 150. Alternatively, or in addition, the computing system 102 filters the video captured by the video recording system 104 after it is stored on the data collection system 150.

Figure 2:
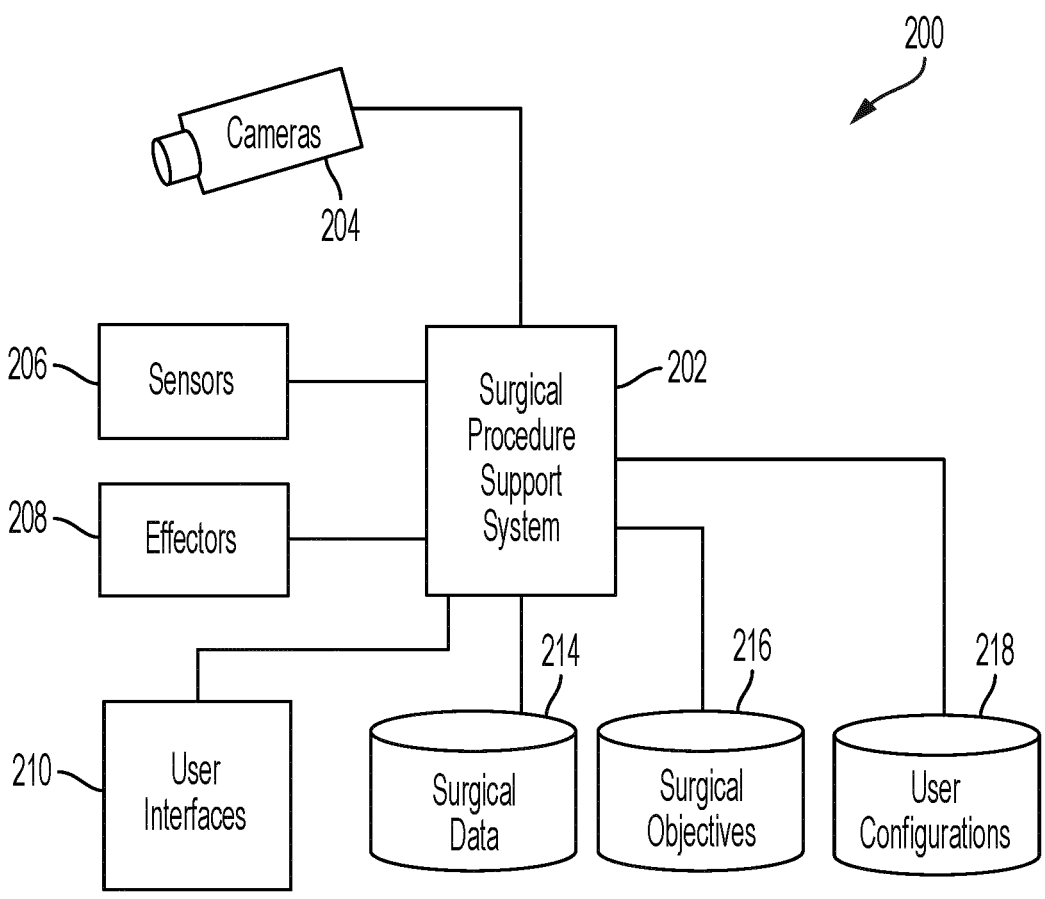
FIG. 2 depicts a surgical procedure system in accordance with one or more aspects.

Turning now to FIG. 2, a surgical procedure system 200 is generally shown in accordance with one or more aspects. The example of FIG. 2 depicts a surgical procedure support system 202 that can include or may be coupled to the system 100 of FIG. 1. The surgical procedure support system 202 can acquire image or video data using one or more cameras 204. The surgical procedure support system 202 can also interface with a plurality of sensors 206 and effectors 208. The sensors 206 may be associated with surgical support equipment and/or patient monitoring. The effectors 208 can be robotic components or other equipment controllable through the surgical procedure support system 202. The surgical procedure support system 202 can also interact with one or more user interfaces 210, such as various input and/or output devices. The surgical procedure support system 202 can store, access, and/or update surgical data 214 associated with a training dataset and/or live data as a surgical procedure is being performed on patient 110 of FIG. 1. The surgical procedure support system 202 can store, access, and/or update surgical objectives 216 to assist in training and guidance for one or more surgical procedures. User configurations 218 can track and store user preferences.

Figure 3:
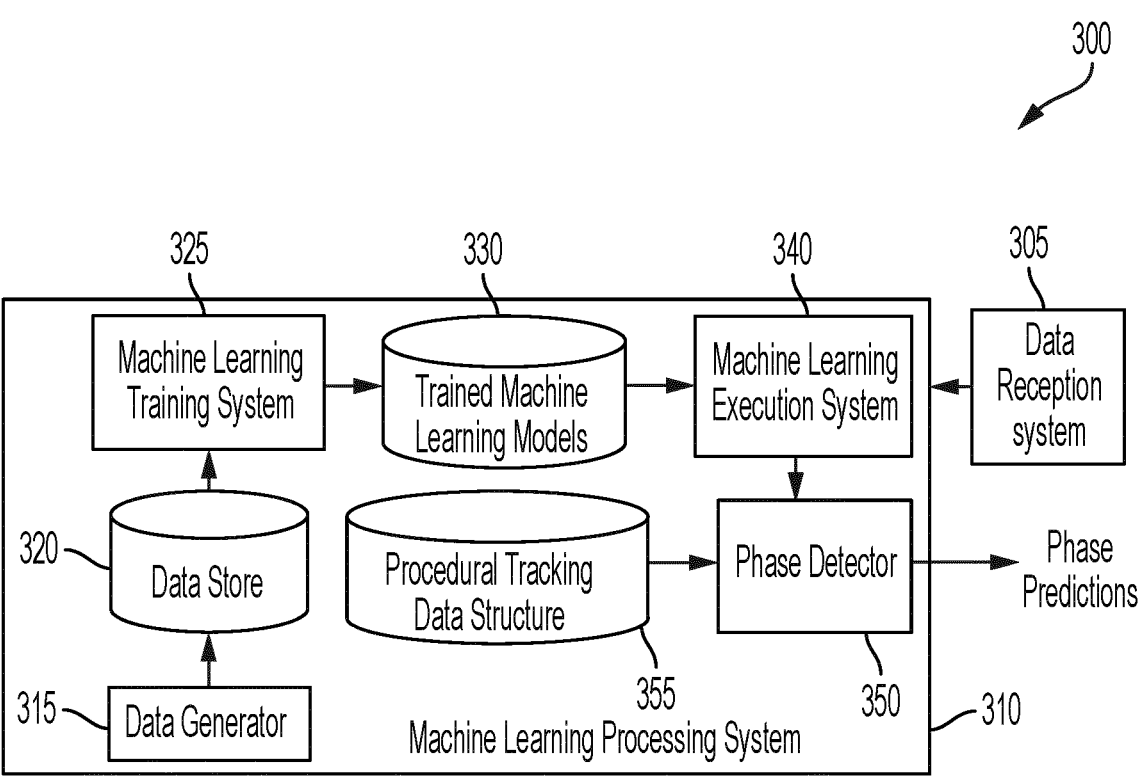
FIG. 3 depicts a system for analyzing video captured by a video recording system according to one or more aspects.

Turning now to FIG. 3, a system 300 for analyzing video and data is generally shown according to one or more aspects. For example, the video and data can be captured from video recording system 104 of FIG. 1. The analysis can result in predicting surgical phases and structures (e.g., instruments, anatomical structures, etc.) in the video data using machine learning. System 300 can be the computing system 102 of FIG. 1, or a part thereof in one or more examples. System 300 uses data streams in the surgical data to identify procedural states according to some aspects.

System 300 includes a data reception system 305 that collects surgical data, including the video data and surgical instrumentation data. The data reception system 305 can include one or more devices (e.g., one or more user devices and/or servers) located within and/or associated with a surgical operating room and/or control center. The data reception system 305 can receive surgical data in real-time, i.e., as the surgical procedure is being performed. Alternatively, or in addition, the data reception system 305 can receive or access surgical data in an offline manner, for example, by accessing data that is stored in the data collection system 150 of FIG. 1.

System 300 further includes a machine learning processing system 310 that processes the surgical data using one or more machine learning models to identify one or more features, such as surgical phase, instrument, anatomical structure, etc., in the surgical data. It will be appreciated that machine learning processing system 310 can include one or more devices (e.g., one or more servers), each of which can be configured to include part or all of one or more of the depicted components of the machine learning processing system 310. In some instances, a part or all of the machine learning processing system 310 is in the cloud and/or remote from an operating room and/or physical location corresponding to a part or all of data reception system 305. It will be appreciated that several components of the machine learning processing system 310 are depicted and described herein. However, the components are just one example structure of the machine learning processing system 310, and that in other examples, the machine learning processing system 310 can be structured using a different combination of the components. Such variations in the combination of the components are encompassed by the technical solutions described herein.

The machine learning processing system 310 includes a machine learning training system 325, which can be a separate device (e.g., server) that stores its output as one or more trained machine learning models 330. The machine learning models 330 are accessible by a model execution system 340. The model execution system 340 can be separate from the machine learning training system 325 in some examples. In other words, in some aspects, devices that "train" the models are separate from devices that "infer," i.e., perform real-time processing of surgical data using the trained machine learning models 330.

Machine learning processing system 310, in some examples, further includes a data generator 315 to generate simulated surgical data, such as a set of virtual images, or record the video data from the video recording system 104, to train the machine learning models 330. Data generator 315 can access (read/write) a data store 320 to record data, including multiple images and/or multiple videos. The images and/or videos can include images and/or videos collected during one or more procedures (e.g., one or more surgical procedures). For example, the images and/or video may have been collected by a user device worn by the actor 112 of FIG. 1 (e.g., surgeon, surgical nurse, anesthesiologist, etc.) during the surgery, a non-wearable imaging device located within an operating room, or an endoscopic camera inserted inside the patient 110 of FIG. 1. The data store 320 is separate from the data collection system 150 of FIG. 1 in some examples. In other examples, the data store 320 is part of the data collection system 150.

Each of the images and/or videos recorded in the data store 320 for training the machine learning models 330 can be defined as a base image and can be associated with other data that characterizes an associated procedure and/or rendering specifications. For example, the other data can identify a type of procedure, a location of a procedure, one or more people involved in performing the procedure, surgical objectives, and/or an outcome of the procedure. Alternatively, or in addition, the other data can indicate a stage of the procedure with which the image or video corresponds, rendering specification with which the image or video corresponds and/or a type of imaging device that captured the image or video (e.g., and/or, if the device is a wearable device, a role of a particular person wearing the device, etc.). Further, the other data can include image-segmentation data that identifies and/or characterizes one or more objects (e.g., tools, anatomical objects, etc.) that are depicted in the image or video. The characterization can indicate the position, orientation, or pose of the object in the image. For example, the characterization can indicate a set of pixels that correspond to the object and/or a state of the object resulting from a past or current user handling. Localization can be performed using a variety of techniques for identifying objects in one or more coordinate systems.

The machine learning training system 325 uses the recorded data in the data store 320, which can include the simulated surgical data (e.g., set of virtual images) and actual surgical data to train the machine learning models 330. The machine learning model 330 can be defined based on a type of model and a set of hyperparameters (e.g., defined based on input from a client device). The machine learning models 330 can be configured based on a set of parameters that can be dynamically defined based on (e.g., continuous or repeated) training (i.e., learning, parameter tuning). Machine learning training system 325 can use one or more optimization algorithms to define the set of parameters to minimize or maximize one or more loss functions. The set of (learned) parameters can be stored as part of a trained machine learning model 330 using a specific data structure for that trained machine learning model 330. The data structure can also include one or more non-learnable variables (e.g., hyperparameters and/or model definitions).

Machine learning model execution system 340 can access the data structure(s) of the machine learning models 330 and accordingly configure the machine learning models 330 for inference (i.e., prediction). The machine learning models 330 can include, for example, a fully convolutional network adaptation, an adversarial network model, an encoder, a decoder, or other types of machine learning models. The type of the machine learning models 330 can be indicated in the corresponding data structures. The machine learning model 330 can be configured in accordance with one or more hyperparameters and the set of learned parameters.

The machine learning models 330, during execution, receive, as input, surgical data to be processed and subsequently generate one or more inferences according to the training. For example, the video data captured by the video recording system 104 of FIG. 1 can include data streams (e.g., an array of intensity, depth, and/or RGB values) for a single image or for each of a set of frames (e.g., including multiple images or an image with sequencing data) representing a temporal window of fixed or variable length in a video. The video data that is captured by the video recording system 104 can be received by the data reception system 305, which can include one or more devices located within an operating room where the surgical procedure is being performed. Alternatively, the data reception system 305 can include devices that are located remotely, to which the captured video data is streamed live during the performance of the surgical procedure. Alternatively, or in addition, the data reception system 305 accesses the data in an offline manner from the data collection system 150 or from any other data source (e.g., local or remote storage device).

The data reception system 305 can process the video and/or data received. The processing can include decoding when a video stream is received in an encoded format such that data for a sequence of images can be extracted and processed. The data reception system 305 can also process other types of data included in the input surgical data. For example, the surgical data can include additional data streams, such as audio data, RFID data, textual data, measurements from one or more surgical instruments/sensors, etc., that can represent stimuli/procedural states from the operating room. The data reception system 305 synchronizes the different inputs from the different devices/sensors before inputting them in the machine learning processing system 310.

The machine learning models 330, once trained, can analyze the input surgical data, and in one or more aspects, predict and/or characterize structures included in the video data included with the surgical data. The video data can include sequential images and/or encoded video data (e.g., using digital video file/stream formats and/or codecs, such as MP4, MOV, AVI, WEBM, AVCHD, OGG, etc.). The prediction and/or characterization of the structures can include segmenting the video data or predicting the localization of the structures with a probabilistic heatmap. In some instances, the one or more machine learning models include or are associated with a preprocessing or augmentation (e.g., intensity normalization, resizing, cropping, etc.) that is performed prior to segmenting the video data. An output of the one or more machine learning models can include image-segmentation or probabilistic heatmap data that indicates which (if any) of a defined set of structures are predicted within the video data, a location and/or position and/or pose of the structure(s) within the video data, and/or state of the structure(s). The location can be a set of coordinates in an image/frame in the video data. For example, the coordinates can provide a bounding box. The coordinates can provide boundaries that surround the structure(s) being predicted. The machine learning models 630, in one or more examples, are trained to perform higher-level predictions and tracking, such as predicting a phase of a surgical procedure and tracking one or more surgical instruments used in the surgical procedure.

While some techniques for predicting a surgical phase ("phase") in the surgical procedure are described herein, it should be understood that any other technique for phase prediction can be used without affecting the aspects of the technical solutions described herein. In some examples, the machine learning processing system 310 includes a phase detector 350 that uses the machine learning models to identify a phase within the surgical procedure ("procedure"). Phase detector 350 uses a particular procedural tracking data structure 355 from a list of procedural tracking data structures. Phase detector 350 selects the procedural tracking data structure 355 based on the type of surgical procedure that is being performed. In one or more examples, the type of surgical procedure is predetermined or input by actor 112. The procedural tracking data structure 355 identifies a set of potential phases that can correspond to a part of the specific type of procedure.

In some examples, the procedural tracking data structure 355 can be a graph that includes a set of nodes and a set of edges, with each node corresponding to a potential phase. The edges can provide directional connections between nodes that indicate (via the direction) an expected order during which the phases will be encountered throughout an iteration of the procedure. The procedural tracking data structure 355 may include one or more branching nodes that feed to multiple next nodes and/or can include one or more points of divergence and/or convergence between the nodes. In some instances, a phase indicates a procedural action (e.g., surgical action) that is being performed or has been performed and/or indicates a combination of actions that have been performed. In some instances, a phase relates to a biological state of a patient undergoing a surgical procedure. For example, the biological state can indicate a complication (e.g., blood clots, clogged arteries/veins, etc.), pre-condition (e.g., lesions, polyps, etc.). In some examples, the machine learning models 330 are trained to detect an "abnormal condition," such as hemorrhaging, arrhythmias, blood vessel abnormality, etc.

Each node within the procedural tracking data structure 355 can identify one or more characteristics of the phase corresponding to that node. The characteristics can include visual characteristics. In some instances, the node identifies one or more tools that are typically in use or availed for use (e.g., on a tool tray) during the phase. The node also identifies one or more roles of people who are typically performing a surgical task, a typical type of movement (e.g., of a hand or tool), etc. Thus, phase detector 350 can use the segmented data generated by model execution system 340 that indicates the presence and/or characteristics of particular objects within a field of view to identify an estimated node to which the real image data corresponds. Identification of the node (i.e., phase) can further be based upon previously detected phases for a given procedural iteration and/or other detected input (e.g., verbal audio data that includes person-to-person requests or comments, explicit identifications of a current or past phase, information requests, etc.).

The phase detector 350 outputs the phase prediction associated with a portion of the video data that is analyzed by the machine learning processing system 310. The phase prediction is associated with the portion of the video data by identifying a start time and an end time of the portion of the video that is analyzed by the machine learning execution system 340. The phase prediction that is output can include an identity of a surgical phase as detected by the phase detector 350 based on the output of the machine learning execution system 340. Further, the phase prediction, in one or more examples, can include identities of the structures (e.g., instrument, anatomy, etc.) that are identified by the machine learning execution system 340 in the portion of the video that is analyzed. The phase prediction can also include a confidence score of the prediction. Other examples can include various other types of information in the phase prediction that is output.

It should be noted that although some of the drawings depict endoscopic videos being analyzed, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

Figure 4:
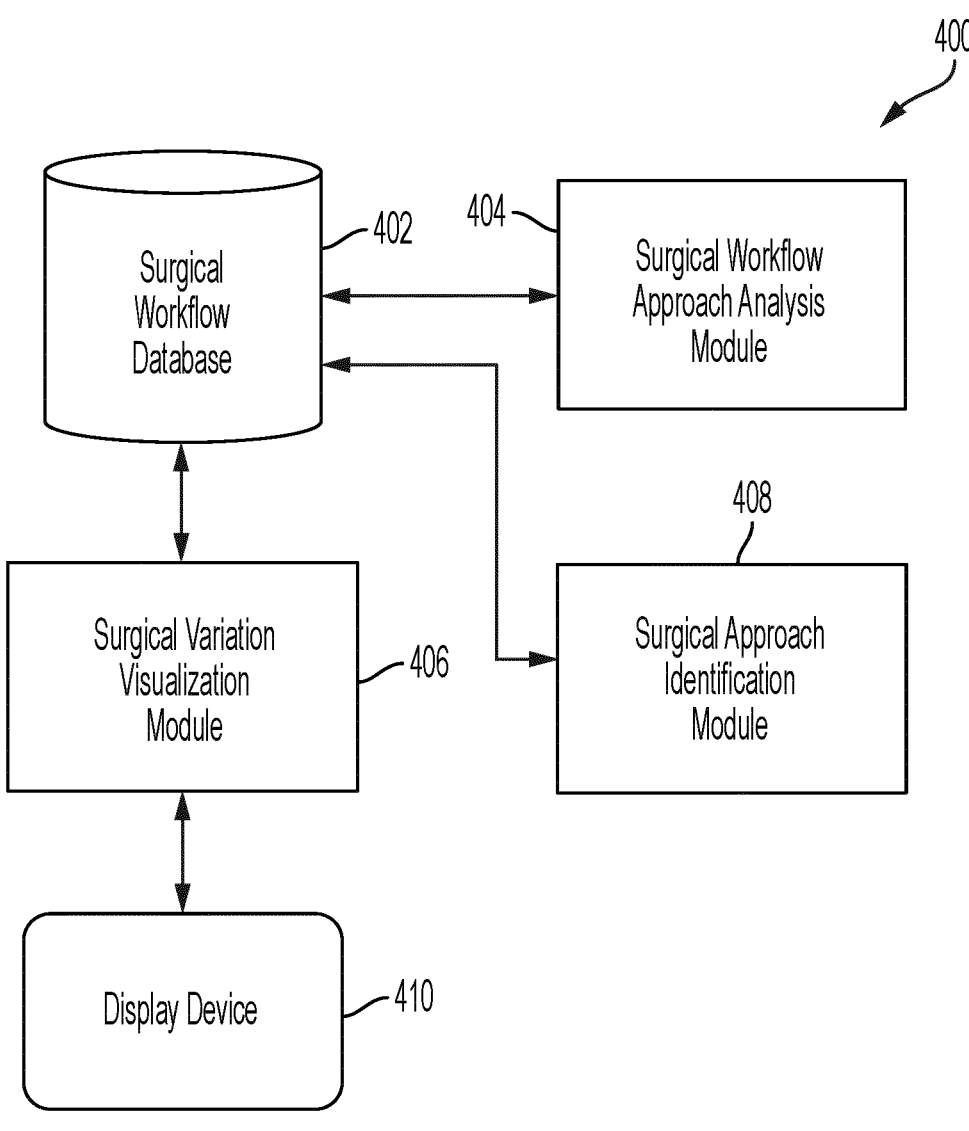
FIG. 4 depicts a block diagram of a data analysis system for identifying variations in surgical approaches according to one or more aspects.

Turning now to FIG. 4, a block diagram of a data analysis system 400 for identifying variations in surgical approaches is generally shown in accordance with one or more aspects. All or a portion of data analysis system 400 can be implemented by CAS system 100 of FIG. 1, and/or by computer system 1000 of FIG. 10. The data analysis system 400 shown in FIG. 4 includes surgical workflow data 402, surgical workflow approach analysis module 404, surgical variation visualization module 406, surgical approach identification module 408, and display device 410. Examples of the processing that can be performed by the modules shown in FIG. 4 are shown below in FIG. 5 and FIG. 6.

The surgical workflow database 402 stores video data captured, for example, by video recording system 104 of FIG. 1 and/or cameras 204 of FIG. 2, which is broken into phases, for example, by machine learning processing system 310 of FIG. 3. According to aspects of the technical solutions described herein, the surgical workflow database 402 is located in a storage device 152 of the data collection system of FIG. 1 or stored as surgical data 214 of FIG. 2. The surgical workflow database 402 includes surgical video data recorded during several iterations of the same medical procedure by one or more different surgical service providers. The display device 410 shown in FIG. 4 can be implemented by any user display device that is accessible to a user who has been granted access to viewing the results of the analysis described herein. Aspects include the display device 410 supporting a graphical user interface (GUI) for outputting graphical data.

All or a portion of the surgical workflow approach analysis module 404, surgical approach identification module 408, and surgical variation visualization module 406 can be implemented by computer instructions being executed by computing system 102 of FIG. 1. Surgical workflow approach analysis module 404 receives surgical workflow data 402 that includes video recordings of multiple surgical procedures of the same type and creates groupings of similar workflows. The video recording, or surgical workflow, of each instance of the particular type of surgical procedure is annotated with phases that have been identified, for example, by machine learning processing system 310 and/or via manual annotation. The annotation can be used to segment a surgical workflow into surgical phases. Further, the surgical workflows are grouped/clustered automatically using machine learning techniques. The grouping can be performed based on one or more factors. The factors can include, for example, but are not limited to, the identified surgical phases in each surgical workflow, medical personnel (e.g., surgeon, staff, trainee/interns, etc.) performing the surgical workflow, hospital/institution where the surgical workflow is being performed, equipment used for the surgical workflow, etc. or a combination thereof. The surgical approach identification module 408 assigns an identifier, automatically using machine learning techniques or via prompted user input, to each grouping of the surgical workflows. Aspects can include that the identifier is descriptive of the type of approach used by the workflows in one or more of the identified groups (e.g., anatomically top-down, systematic approach, etc.). The identifier of each cluster, or group, of surgical workflows can be stored in the surgical workflow database 402 along with pointers to surgical workflows belonging to each group.

The surgical variation visualization module 406 shown in FIG. 4 can provide authorized users with different views via display device 410 of the analysis of the data stored in the surgical workflow database 402. For example, each grouping can be shown in a different color, or surgical workflows capturing surgeries by different surgical service providers can be shown in different colors. Examples are shown below in FIG. 8 and FIG. 9. In one or more embodiments of the present invention, all, or a portion, of the surgical variation visualization module 406 is executing by a processor located on a user device (e.g., a personal computer, laptop, mobile phone, etc.) and the display device 410 is located on or attached to the user device. All or portion of the surgical workflow database 402 can be accessed by the surgical variation visualization module 406 via one or more network connections.

The computing environment of FIG. 4 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various aspects.

It is to be understood that the block diagram of FIG. 4 is not intended to indicate that system 400 is to include all of the components shown in FIG. 4. Rather, the system 400 can include any appropriate fewer or additional components not illustrated in FIG. 4, such as but not limited to one or more additional display devices 410 and/or surgical workflow databases 402. In addition, the components shown in FIG. 4 may be arranged differently. For example, the surgical workflow approach analysis module 404 and the surgical approach identification module 408 may be located on different computer servers, or they may be part of the same processing unit.

Turning now to FIG. 5, a flowchart of a method 500 for identifying variations in surgical approaches is generally shown in accordance with one or more aspects. All or a portion of method 500 can be implemented, for example, by all or a portion of CAS system 100 of FIG. 1, system 200 of FIG. 2, system 300 of FIG. 3, and/or system 400 of FIG. 4. Method 500 shown in FIG. 5 includes a pipeline that can be used to extract surgical approaches.

Surgical workflow data (e.g., surgical video) is acquired or received, at block 502 of FIG. 5. At least a portion of the surgical workflow data can be acquired, for example, from data collection system 150 of FIG. 1. The acquired surgical workflow data pertains to a single type of surgical procedure or a group of similar procedures, and may include workflow data from multiple surgical service providers such as multiple different surgeons and/or multiple institutions (e.g., hospitals) and by different surgeons. The surgical workflow data includes video data, e.g., laparoscopic video, for each iteration of the surgical procedure. The dataset acquired at block 502 can include additional data for each surgical procedure, such as but not limited to hospital identification/characteristics (e.g., location, frequency of performing the surgical procedure, etc.), surgeon identification/characteristics (e.g., years in practice, training, experience with the surgical procedure, etc.), and/or patient identification/characteristics (e.g., age, height, weight, etc.). At block 504, the surgical video is segmented into surgical phases using, for example, visual cues in the video. For example, the visual cues can include but are not limited to surgical instruments, anatomical approaches, etc., in the video. The segmenting can include annotating the video and breaking the video up into multiple segments based on the annotating. According to aspects of the technical solutions described herein, the duration of the segments can also be used to identify surgical approaches. In addition, certain surgical phases can be repeated in the same case.

As used herein, the term "case" refers to one iteration of the surgical procedure, that is, a single surgery represented by a single surgical workflow. The surgical workflow data, or dataset, acquired at block 502 can include several cases (hundreds or even thousands) of a particular type of surgical procedure obtained from different surgical service providers. The surgical workflow data can also be obtained for a single surgical service provider to analyze consistency and/or approaches used by the single surgical service provider.

At block 506 of FIG. 5, invalid surgical workflows are removed from the dataset. Invalid surgical workflows are workflows that are incomplete, that is, they do not include phases that are necessary to complete the surgical procedure. Input from medical experts can be used to determine which phases are necessary to complete the medical procedure. Each surgical workflow can be scanned by the computer for the required phases, and surgical workflows can be removed at block 506 if they are missing a required phase. In accordance with one or more aspects, the validation preformed at block 506 includes the use of logical "rules" provided by medical experts that allow the detection of sequences of phases that are impossible. This allows the exclusion of some possible annotation errors and things like videos that contain two cases instead of one.

Processing continues at block 508 with grouping the surgical workflows into similar surgical workflows using a clustering algorithm. Aspects of technical solutions herein compare distance matrices, defined for all case pairs using several metrics, which capture content, temporal, transition, and edit similarity. Further, clustering techniques can be used to identify groups of similar surgical workflows. Pattern recognition techniques can be applied to determine associated approaches found in the performance of the surgical procedures. The optimal distance metric, algorithm, and associated parameters can be identified using clustering efficiency and classification evaluation metrics. Using this analysis, key approaches that each surgical service provider in the dataset had adopted are identified. For example, spectral clustering with an edit similarity metric can be used to analyze the datasets. Edit distances can be computed using techniques such as dynamic time warping, Levenshtein, Optimal String Alignment, and Damerau Levenshtein. Alternatively, graphical distances can be computed and used for the analysis. The graphical distances can be computed using Adjacency, Graph Matching, or other such techniques. Further yet, set distances can also be computed and used to analyze the datasets. The set distances can be computed using techniques such as Jaccard, Chi-Squared, etc.

In one or more examples, multiple types of distance measures are computed. Different distance measures can represent different types of variation between workflows. In some examples, a distance matrix is constructed to analyze the entire input dataset. An example of a process for performing the clustering of block 508 of FIG. 5 is shown below in FIG. 6. After the processing at block 508 is completed, processing continues at blocks 510 and 512.

At block 512 of FIG. 5, the top surgical approaches which are unique to each group are determined using subsequence and substring identification which can indicate the different approaches. The surgical approaches can be identified by the substrings and subsequences that occur in the surgical workflows. At block 514, surgical approaches are named by medical experts using well-known medical terminology along with further medical insight unique to each approach to understand the clinical significance. The detected approaches within each group can indicate differences or variations in the approaches for the various surgical procedures. For example, various clusters can be identified that represent approaches such as, but are not limited to, an anatomically top-down approach, a retrocolic anastomosis approach, and a systematic approach.

At block 510, surgical variation is visualized in three dimensions (3D), as shown, for example, in FIG. 8 below, by computing the UMap representation of the distance matrix. Each point in the visualization is a surgical workflow, and workflows closer together in space are increasingly similar. Structure in the dataset can be visualized by coloring or shading in the clusters with the unsupervised clustering labels that are applied by the system to distinguish between the clusters (e.g., "Approach 1" or "Group 1", etc.). Note that the same approach can be used to visualize the distance matrix in two dimensions (2D). In addition, one cluster can have multiple approaches.

The processing shown in FIG. 5 is not intended to indicate that the operations are to be executed in any particular order or that all of the operations shown in FIG. 5 are to be included in every case. Additionally, the processing shown in FIG. 5 can include any suitable number of additional operations.

Figure 6:
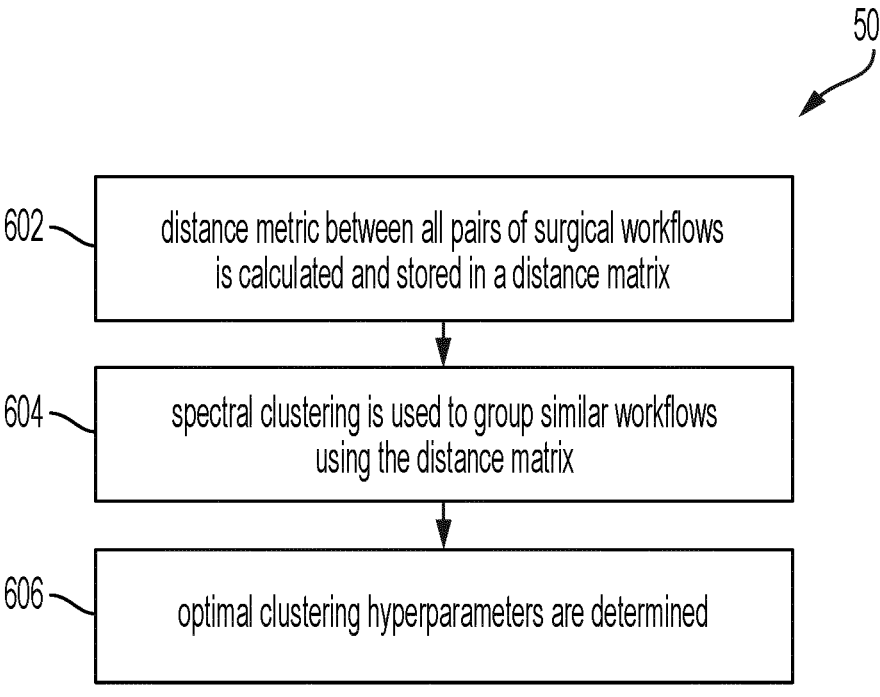
FIG. 6 depicts a flowchart of a method for grouping surgical workflows into similar workflows according to one or more aspects.

Turning now to FIG. 6, a flowchart of a method 508 for grouping surgical workflows into similar workflows using a clustering algorithm is generally shown in accordance with one or more aspects. At block 602 of FIG. 6, a distance metric between all pairs of surgical workflows remaining in the dataset after the processing at block 506 of FIG. 5 is calculated and stored in a distance matrix.

A simplified example includes five surgical workflows or cases, each segmented into a plurality of phases. "A", "B", "C", and "D" each represent a different phase of a surgical procedure. As shown below, Surgical Workflow 0 is segmented into an ordered sequence of phases that includes "ABCDADB." "ABCDADB" is a symbolic representation of Surgical Workflow 0

Turning now to the example, where a dataset that includes five surgical workflows is analyzed. In this example, the phases include phases A, B, C, and D and the sequences follow:

Surgical Workflow 0: A B C D A B D,
Surgical Workflow 1: A B C B D A B D,
Surgical Workflow 2: A B C B A B D,
Surgical Workflow 3: D A D B A B C, and
Surgical Workload 4: D A D C B A B C.

The distance metric can be calculated using the Levenshtein distance, which is a metric for measuring the difference between two sequences. The Levenshtein distance between two words, or sequences, is the minimum number of single-character edits (insertions, deletions, or substitutions) required to change one word into the other. In this example, the distance matrix calculated using the Levenshtein distance results in:

| | Surgical Work-flow 0 | Surgical Work-flow 1 | Surgical Work-flow 2 | Surgical Work-flow 3 | Surgical Work-flow 4 |
|---|---|---|---|---|---|
| Surgical Workflow 0 | 0 | 1 | 1 | 5 | 5 |
| Surgical Workflow 1 | 1 | 0 | 1 | 5 | 5 |
| Surgical Workflow 2 | 1 | 1 | 0 | 4 | 4 |
| Surgical Workflow 3 | 5 | 5 | 4 | 0 | 1 |
| Surgical Workflow 4 | 5 | 5 | 4 | 1 | 0 |

The distance matrix calculated at block 502 can be stored, for example, in surgical workflow database 402 of FIG. 4.

At block 604 of FIG. 6, spectral clustering is used to cluster, or group, similar workflows using the computed distance matrix. Continuing with the example, based on the above distance matrix, the surgical workflows can be divided into two clusters, the first cluster including:

Surgical Workflow 0: A B C B A B D,
Surgical Workflow 1: A B C B D A B D, and
Surgical Workflow 2: A B C B A B D;
and the second cluster including:
Surgical Workflow 3: D A D B A B C, and
Surgical Workflow 4: D A D C B A B C.

Figure 7:
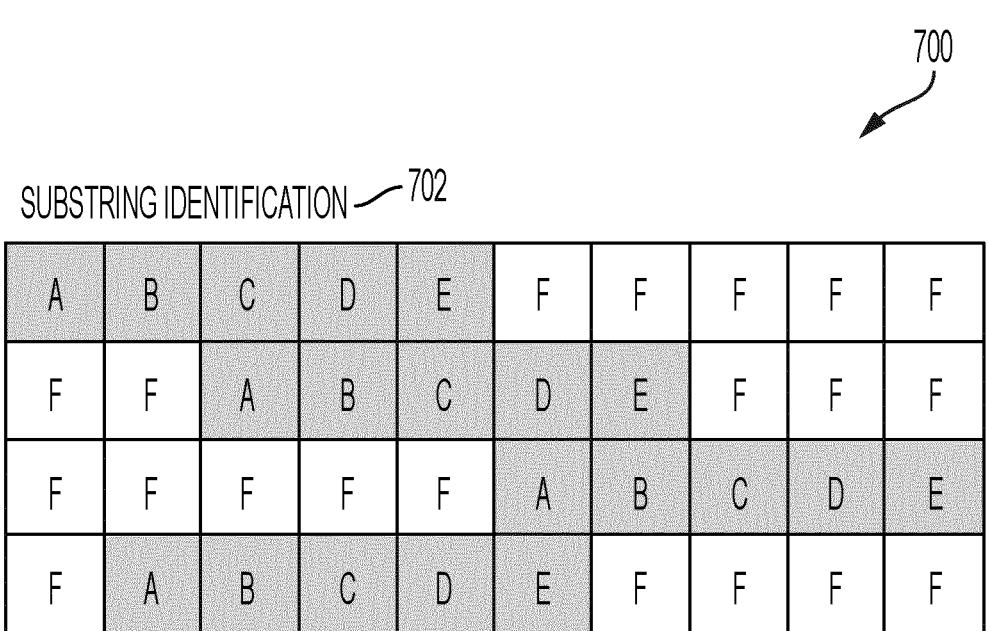
FIG. 7 depicts a block diagram of surgical workflow phase substrings and subsequences according to one or more aspects.

Turning now to FIG. 7, a block diagram 700 of example surgical workflow phase substrings and subsequences are generally shown. In FIG. 7, each box represents a phase, and a row of blocks represents a surgical procedure or surgical workflow. The phases are depicted in sequence of operation, and the blocks are assigned visual attributes according to a type of the phase. For example, "Creation of Jejuno-jejunostomy" is depicted as "A", "Creation of Gastro-jejunostomy"

as "B", and "Closure of Mesenteric Defects" as "C". Other visual attributes, such as different colors or different shadings, or differently shaped graphics, can be used in other display examples.

Matching substrings include the same consecutive phases in the same order. Substring identification block 702 includes four surgical workflows that each include the substring "ABCDE." Matching subsequences include the same phase in the same order, but the phases do not need to be consecutive. Subsequence identification block 704 of FIG. 7 includes four surgical workflows that each include the subsequence "ABCDE."

Turning back to the example, the two metrics determined at block 606 of FIG. 6 are determined as follows. The longest unique substring is identified in each cluster. The first cluster includes two substrings: "ABD" and "ABC"; and the second cluster includes two substrings: "BABC" and "DAD." The substring "ABC" in the first substring is eliminated from the calculation because it occurs in both the first cluster and the second cluster, that is, it is not unique to the cluster that it comes from. The longest unique substring in the first cluster is "ABD" having a length of three, and the longest unique substring in the second cluster is "BABC" having a length of four Next, in accordance with aspects of the technical solutions described herein, the maximal unique subsequences are calculated for each of the clusters. The first cluster includes the following subsequences: "ABCD", "ABCBD", "ABCAD", and "ABCABD"; and the second cluster includes the following subsequences: "DADBC", "DADBBC", "DADBAC", and "DADBABC." In this case, all the subsequences are unique to the cluster that they come from, so none of them are eliminated from consideration. There are generally many candidate subsequences, and these can be reduced by removing subsequences that are also subsequences of other subsequences, leaving what are commonly called maximal subsequences. This results in far fewer subsequences per cluster. The maximal unique subsequence in the first cluster is "ABCABD" and the maximal unique subsequence in the second subsequence is "DADBABC." The combination of the longest unique substrings and maximal unique subsequences can be used to define the approaches in a given cluster.

Figure 11:
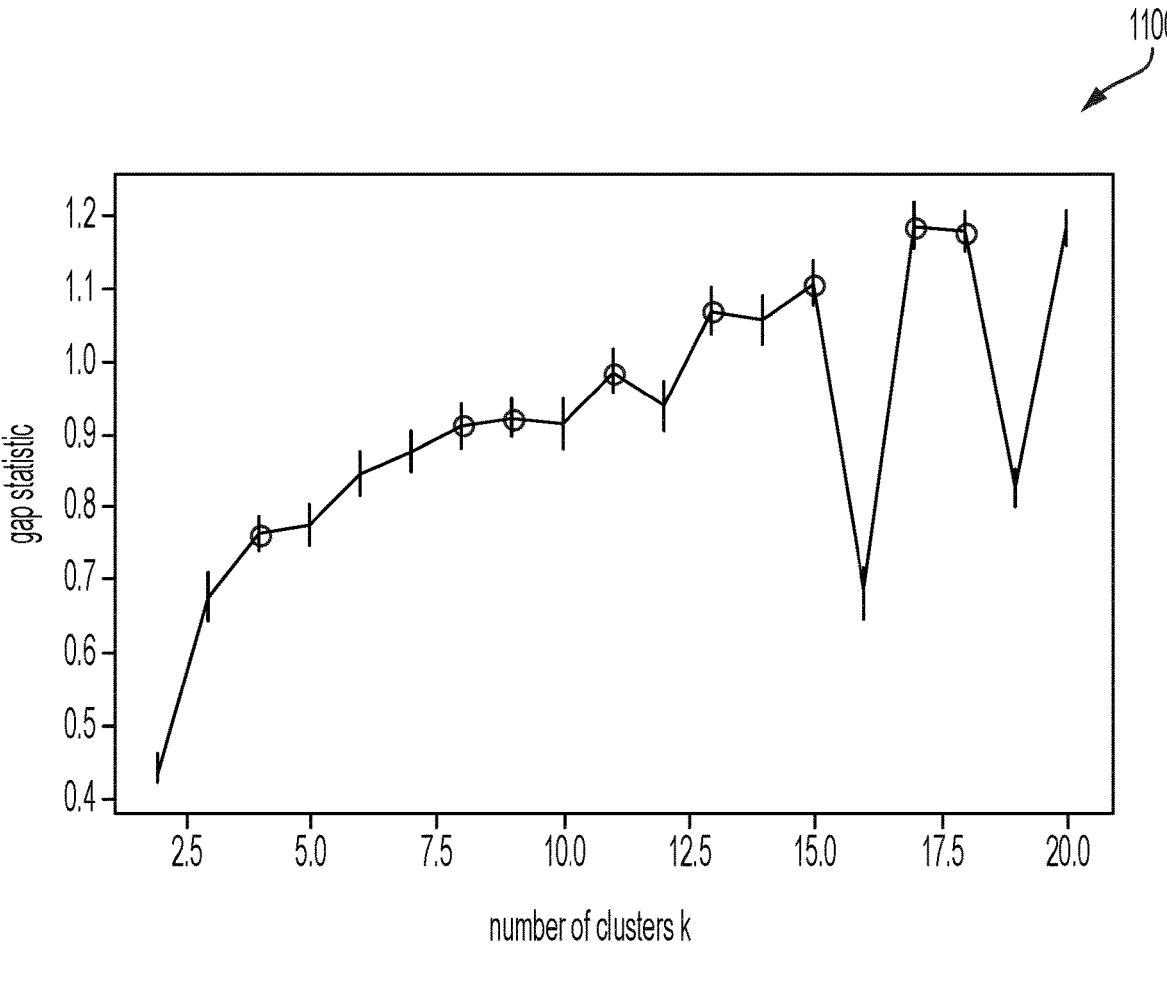
FIG. 11 depicts an example of a gap curve in accordance with one or more aspects.

At block 606 of FIG. 6, optimal clustering hyperparameters are determined. In accordance with one or more embodiments of the present invention, the clustering hyperparameter to be optimized is k, the number of clusters to divide the data into. A common approach for determining k is to use the gap statistic but this cannot be applied to sequential data in its original form. In order to apply it to surgical workflow data, random surgical workflows need to be generated as a reference data set to compare against. In accordance with one or more embodiments of the present invention, a Markov chain model is used to learn transition probabilities from the data and then to generate random sequences for the reference dataset. Once the reference dataset has been generated, the gap function can be plotted for multiple values of k and the expression: Gap(k)>=Gap (k+1)−standard error is used to identify values of k to use. FIG. 11 depicts an example of a gap curve 1100 with the values of k matching the criteria highlighted. The smallest or second smallest value of k can be selected and represent different possible levels of detail.

According to aspects of the technical solution described herein, the processing shown in FIG. 6 includes calculating distance measurements to create a distance matrix for the workflows in the dataset. A clustering algorithm is also used to find structure in the dataset. The distance matrix can be visualized by surgical variation visualization module 406 of FIG. 4, for example, with dimensional reduction techniques and coloring data according to the group, or cluster, that it belongs to in order to highlight differences between approaches used by surgical service providers. In some examples, the distance matrix is depicted in a format to aid interpretation by a human operator (e.g., visual representation). The distance matrix and/or clusters can be visualized or displayed to a user via a display device such as display device 410 of FIG. 4.

The processing shown in FIG. 6 is not intended to indicate that the operations are to be executed in any particular order, or that all of the operations shown in FIG. 6 are to be included in every case. Additionally, the processing shown in FIG. 6 can include any suitable number of additional operations.

Figure 8:
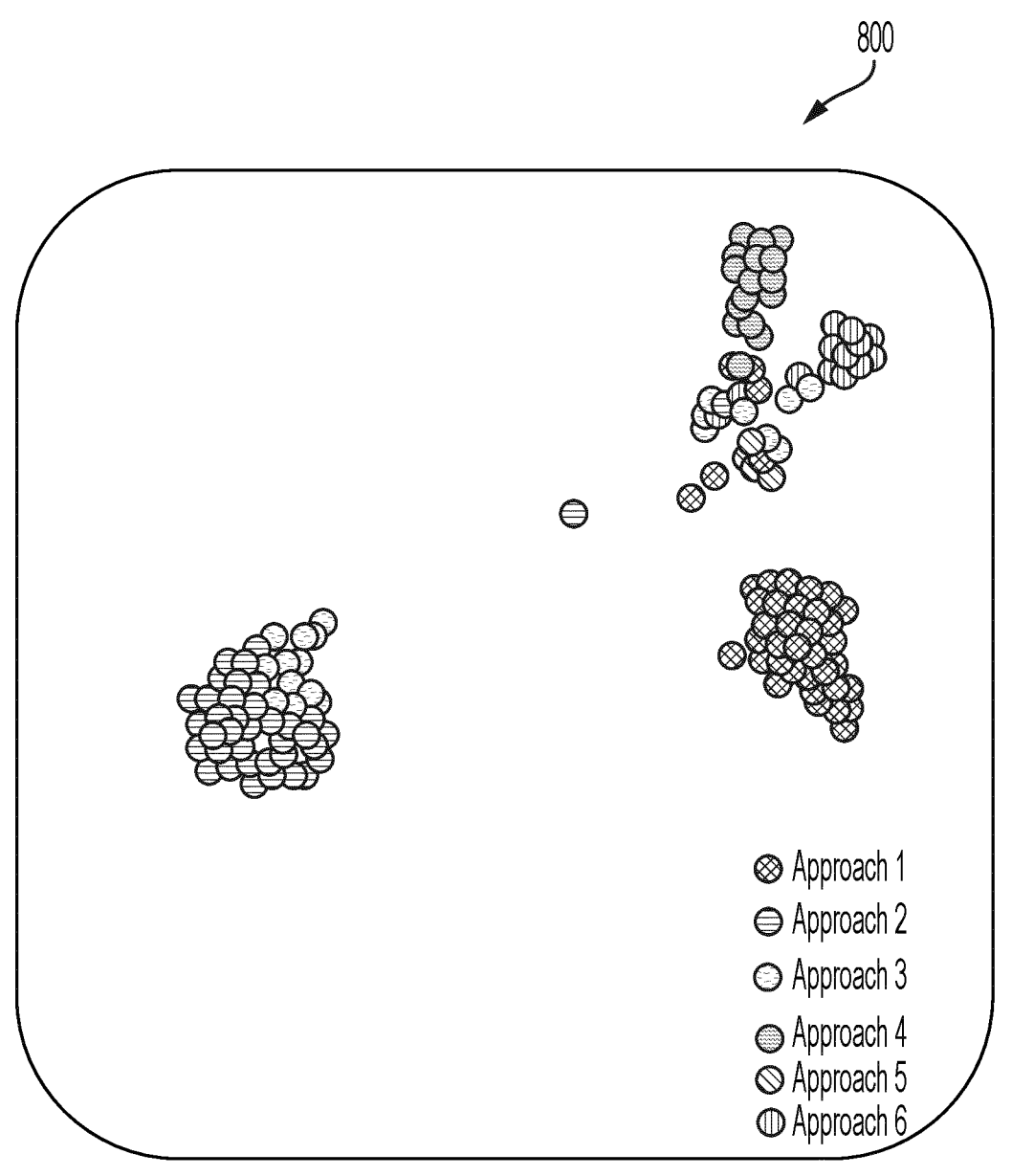
FIG. 8 depicts a visualization of surgical approaches according to one or more aspects.

Turning now to FIG. 8, a visualization 800 of surgical approaches is generally shown in accordance with one or more aspects. The visualization 800 shown in FIG. 8 is a UMap representation of the distance matrix for the workflows in the dataset that can be displayed, for example, on display device 410 of FIG. 4. The UMap representation is just one example of a distance matrix visualization that can be utilized by one or more embodiments of the present invention. Other representations that can be utilized can include, but are not limited to: MDS, t-SNE, and Voronoi Diagrams. Each of the surgical workflows is shaded to indicate which group it belongs with based, for example, on the processing performed in block 508 of FIG. 5. As shown in FIG. 8, the groups are given generic labels: Approach 1, Approach 2, Approach 3, Approach 4, Approach 5, and Approach 6. It should be noted that one clustering group can have multiple approaches. Each point in the visualization is a surgical workflow, and workflows closer together in space are increasingly similar. Though the visualization 800 shown in FIG. 8 is in black and white, it will be appreciated that the visualization can be in color and include any type of graphics. Structure in the dataset can be visualized by coloring or shading in the clusters with the unsupervised clustering labels that are applied by the system to distinguish between the clusters (e.g., "Approach 1" or "Group 1", etc.).

Figure 9:
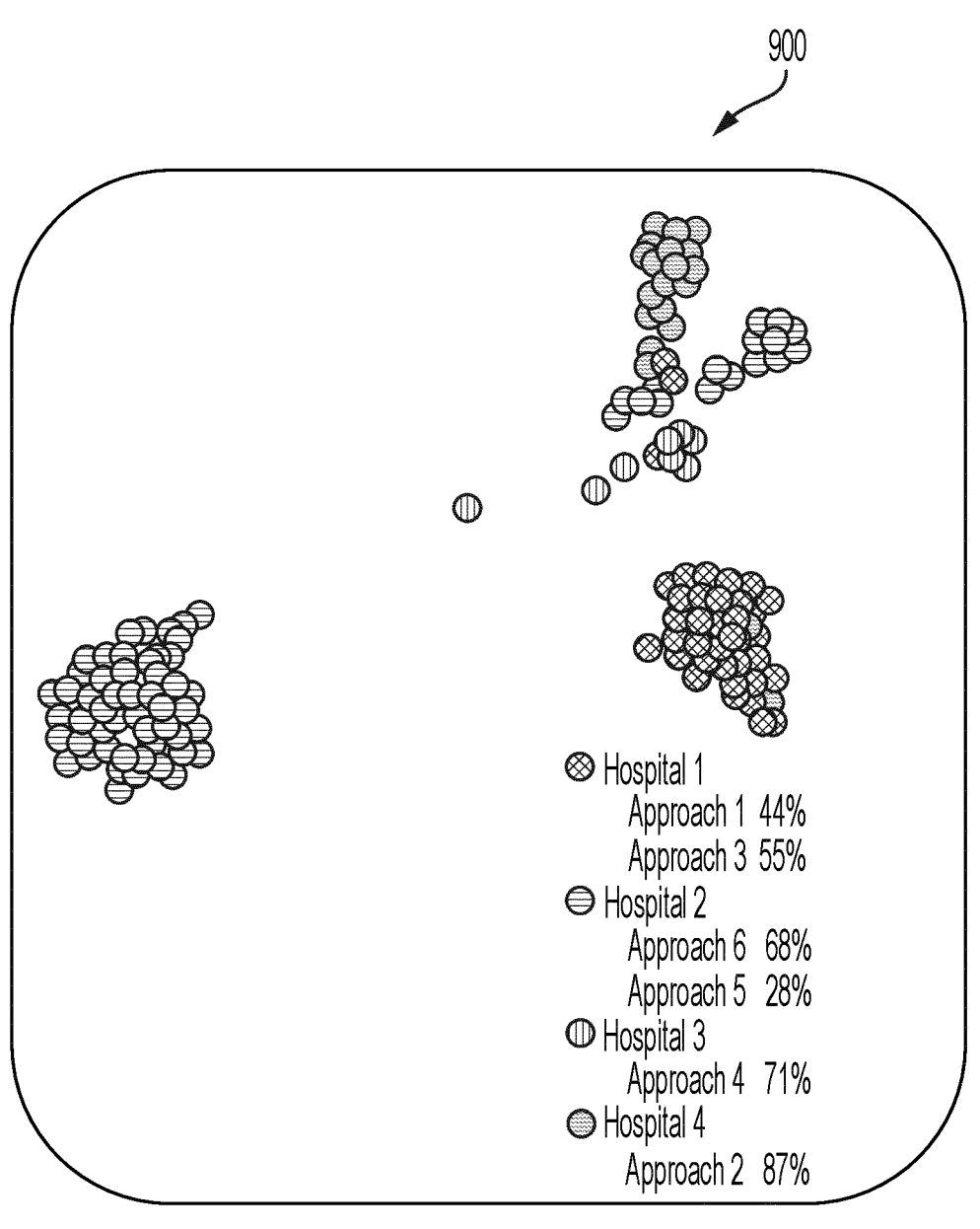
FIG. 9 depicts a visualization of surgical approaches used by different surgical providers according to one or more aspects.

Turning now to FIG. 9, a visualization 900 of surgical approaches used by different surgical providers is generally shown in accordance with one or more aspects. The visualization 900 shown in FIG. 9 can be displayed, for example, on display device 410 of FIG. 4. As shown in FIG. 9, the points in the visualization 900 are shaded to indicate which surgical service provider (in this case, a hospital) performed the procedure. The visualization 900 shown in FIG. 9 can be used to identify the different approaches used by the surgical service providers.

Figure 12:
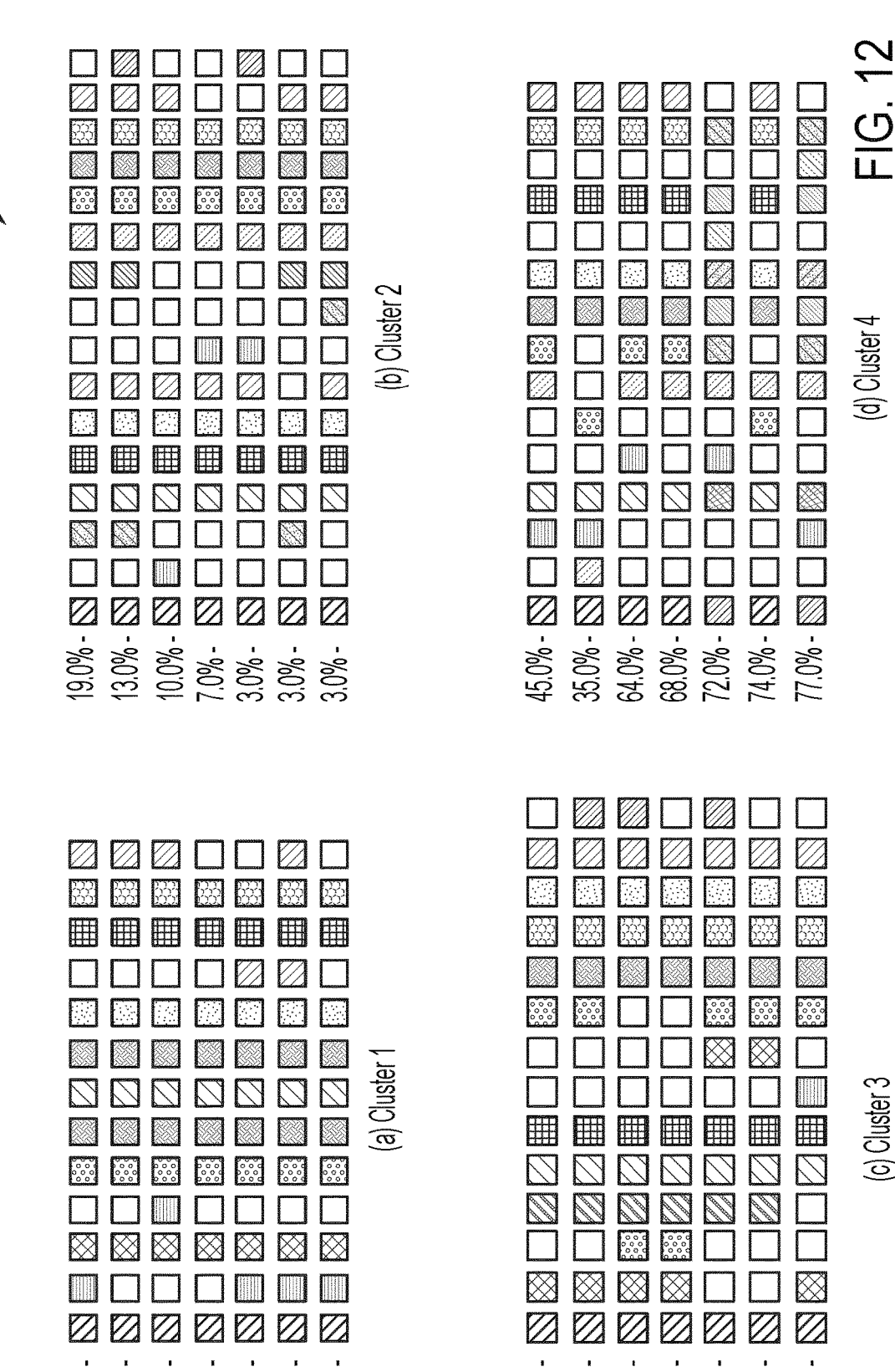
FIG. 12 depicts an example of a visualization of surgical approaches in accordance with one or more aspects.

The visualization 1200 shown in FIG. 12 shows the seven most frequent workflows for each cluster. The maximal patterns have been highlighted to provide more context. In addition, in according to aspects the workflows are aligned so that each column always contains the same phase by adding spacing as indicated by the presence of the unshaded squares. The cumulative percentage of the cluster those workflows represent is also displayed. In order to visualize the identified subsequences or substrings making up a surgical approach the visualization 1220 of FIG. 12 can be used. The most common workflows in a cluster are displayed in order and the phases making up the subsequences or substrings in an approach are highlighted. In this way it can be clearly seen which are the characteristic phases and orderings in a cluster. Further the difference in approach between clusters is also visible allowing workflow variations to be described.

Figure 15:
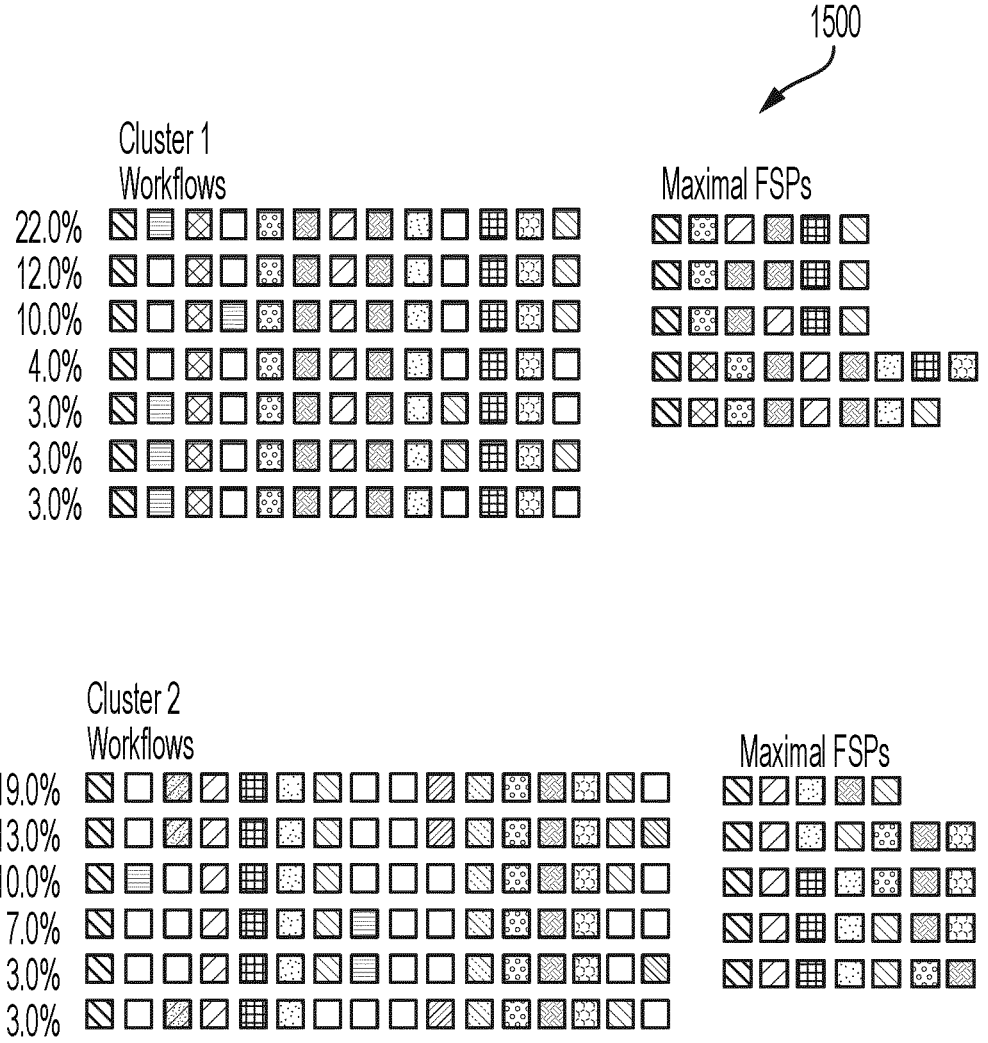
FIG. 15 depicts an example of a visualization of surgical approaches and their maximal frequent sequential patterns (FSPs) in accordance with one or more aspects.
Figure 16:
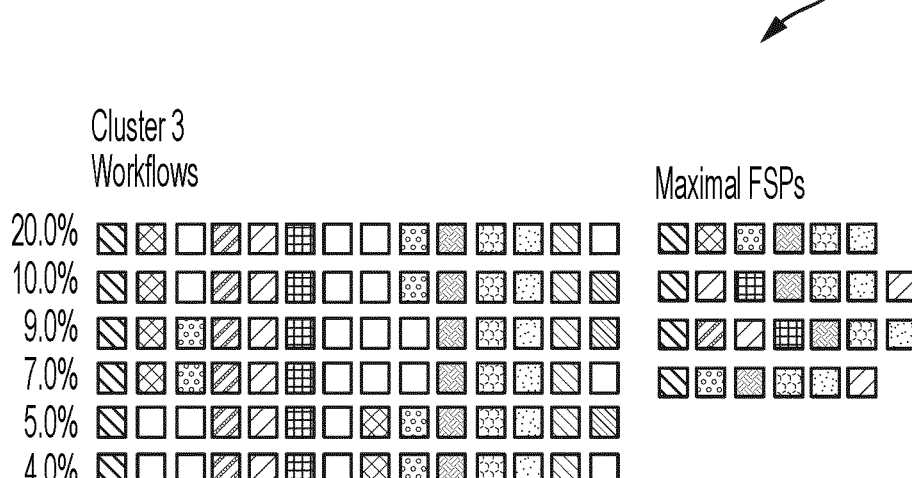
FIG. 16 depicts an example of a visualization of surgical approaches and their maximal frequent sequential patterns (FSPs) in accordance with one or more aspects.
Figure 17:
FIG. 17 depicts a key to the shadings used in the visualizations.

The visualizations 800 900 1200 1300 1400 1500 1600 shown in FIG. 8, FIG. 9, FIG. 12, FIG. 13, FIG. 14, FIG. 15, and FIG. 16 respectively as well as the key 1700 of FIG. 17, are examples of the type of data that may be generated and displayed to a user. FIG. 17 depicts a key 1700 that correlates the shading shown in the visualizations 800 900 1200 1300 1400 1500 1600 to surgical phases. In according to aspects, a graphical representation of the identified surgical approaches (or other data) is output for display on a display device. User input may be received via a user interface of the graphical representation and a second graphical representation including for example, providers that use one or more of the identified surgical approaches, may be output for display on the display device. In this manner, the visualization is interactive and can be modified based on input from a user. One skilled in the art will appreciate that any number of different visualizations containing different data and in different formats can be provided by the surgical variation visualization module 406 of FIG. 4 based on contents of the surgical workflow data for output to display device 410 of FIG. 4.

Aspects of the technical solutions described herein provide the ability to determine a correlation between surgical approaches and surgical service providers. Accordingly, a variation among the service providers can be determined, and in some cases, visualized. In addition, for each hospital, the main surgical approaches used as well as key differentiators for each hospital/approach can be determined. For example, a surgical dataset can be analyzed to determine that for cases performed by Hospital 4: Creation of Jejunojejunostomy is done much later than Creation of Gastrojejunostomy; further, Closure of Mesenteric Defects is done in the middle and at the end of the operation.

Aspects of the technical solutions described herein compare distance matrices, defined for all case pairs using several metrics, which capture content, temporal, transition, and edit similarity. In addition, clustering techniques can be used to classify groups of similar surgical workflows. Pattern recognition techniques are applied to determine associated approaches found in the performance of the surgical procedures. The optimal distance metric, algorithm, and associated parameters are identified using clustering efficiency and classification evaluation metrics. Using this analysis, key approaches that each surgical service provider in the dataset has utilized can be identified.

Technical solutions described herein facilitate computing and using edit distance measures to identify surgically meaningful approaches from a multi-institution dataset, even with granular annotations. Hospitals in the dataset may have two or more different approaches identified, without knowing the reasons why one approach is chosen over the other. Further, the technical solutions described herein can facilitate identifying surgical approaches and their correlation with durations (of surgical procedures/phases) and surgical outcomes.

A fundamental step in the effort to analyze and standardize surgical practice is understanding the impact of surgical workflows on clinical outcome measures. Surgical workflow refers to the order in which surgical objectives are executed in a surgical case. Noise and minor variations between cases can lead to an intractable number of workflows in a dataset of surgical cases. Technical solution described herein provide a methodology for extracting a small number of surgical approaches to represent a dataset of workflows. Each surgical case can be segmented into surgical objectives to get workflows. Levenshtein distance can be used to compute all pairwise distances between the workflows and spectral clustering can be applied to find clusters of similar cases with the expectation that each cluster has its own charac- teristic approaches. The number of clusters can be deter- mined by the gap statistic with a reference null model provided by a Markov chain. Sequential pattern mining combined with a custom uniqueness constraint can then be used to extract key approaches for each cluster.

Technical solutions described herein can identity key approaches in a clustered dataset, where each cluster is characterized by a distinctive approaches. The characteristic approaches can be assessed by a medical professional famil- iar with the procedure to describe the main clinical features of each cluster. Technical solutions including measurable improvements in surgical interventions can be achieved using one or more embodiments of the present invention to objectively quantifying the relationship between a surgical workflow and patient outcomes. One or more embodiments of the present invention provide a methodology that clusters cases according to their surgical workflow and allows these clusters to be labelled and described. These key surgical approaches can then be used to analyze any potential impact on outcome data.

Technical solutions described herein be used to provide measurable improvements in surgical interventions by objectively quantifying the relationship between a surgical workflow and patient outcomes. As described herein, cases are clustered to their surgical workflow and these clusters can be interpreted clinically. Characteristic surgical work- flows can be used to analyze any potential impact on outcome data.

Figure 10:
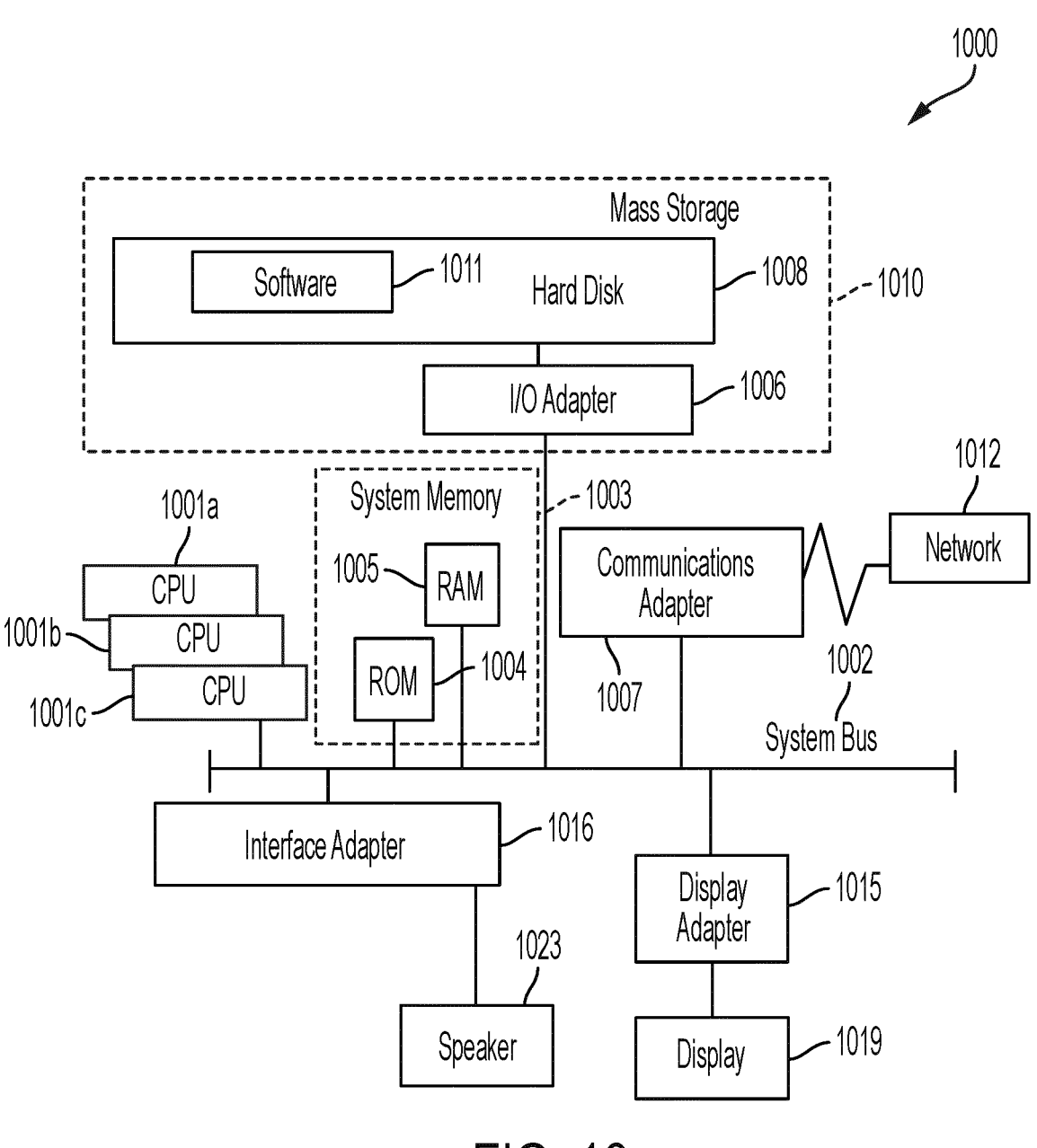
FIG. 10 depicts a computer system in accordance with one or more aspects.

Turning now to FIG. 10, a computer system 1000 is generally shown in accordance with an aspect. The computer system 1000 can be an electronic computer framework comprising and/or employing any number and combination of computing devices and networks utilizing various com- munication technologies, as described herein. The computer system 1000 can be easily scalable, extensible, and modular, with the ability to change to different services or reconfigure some features independently of others. The computer system 1000 may be, for example, a server, desktop computer, laptop computer, tablet computer, or smartphone. In some examples, computer system 1000 may be a cloud computing node. Computer system 1000 may be described in the general context of computer-executable instructions, such as program modules, being executed by a computer system. Generally, program modules may include routines, pro- grams, objects, components, logic, data structures, and so on that perform particular tasks or implement particular abstract data types. Computer system 1000 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 10, the computer system 1000 has one or more central processing units (CPU(s)) 1001*a*, 1001*b*, 1001*c*, etc. (collectively or generically referred to as pro- cessor(s) 1001). The processors 1001 can be a single-core processor, multi-core processor, computing cluster, or any number of other configurations. The processors 1001, also referred to as processing circuits, are coupled via a system bus 1002 to a system memory 1003 and various other components. The system memory 1003 can include one or more memory devices, such as read-only memory (ROM) 1004 and a random access memory (RAM) 1005. The ROM 1004 is coupled to the system bus 1002 and may include a basic input/output system (BIOS), which controls certain basic functions of the computer system 1000. The RAM is read-write memory coupled to the system bus 1002 for use by the processors 1001. The system memory 1003 provides temporary memory space for operations of said instructions during operation. The system memory 1003 can include random access memory (RAM), read-only memory, flash memory, or any other suitable memory systems.

The computer system 1000 comprises an input/output (I/O) adapter 1006 and a communications adapter 1007 coupled to the system bus 1002. The I/O adapter 1006 may be a small computer system interface (SCSI) adapter that communicates with a hard disk 1008 and/or any other similar component. The I/O adapter 1006 and the hard disk 1008 are collectively referred to herein as a mass storage 1010.

Software 1011 for execution on the computer system 1000 may be stored in the mass storage 1010. The mass storage 1010 is an example of a tangible storage medium readable by the processors 1001, where the software 1011 is stored as instructions for execution by the processors 1001 to cause the computer system 1000 to operate, such as is described hereinbelow with respect to the various Figures. Examples of computer program product and the execution of such instruction is discussed herein in more detail. The commu- nications adapter 1007 interconnects the system bus 1002 with a network 1012, which may be an outside network, enabling the computer system 1000 to communicate with other such systems. In one aspect, a portion of the system memory 1003 and the mass storage 1010 collectively store an operating system, which may be any appropriate operat- ing system to coordinate the functions of the various com- ponents shown in FIG. 10.

Additional input/output devices are shown as connected to the system bus 1002 via a display adapter 1015 and an interface adapter 1016 and. In one aspect, the adapters 1006, 1007, 1015, and 1016 may be connected to one or more I/O buses that are connected to the system bus 1002 via an intermediate bus bridge (not shown). A display 1019 (e.g., a screen or a display monitor) is connected to the system bus 1002 by a display adapter 1015, which may include a graphics controller to improve the performance of graphics- intensive applications and a video controller. A keyboard, a mouse, a touchscreen, one or more buttons, a speaker, etc., can be interconnected to the system bus 1002 via the interface adapter 1016, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 10, the computer system 1000 includes processing capability in the form of the processors 1001, and storage capability including the system memory 1003 and the mass storage 1010, input means such as the buttons, touchscreen, and output capability including the speaker 1023 and the display 1019.

In some aspects, the communications adapter 1007 can transmit data using any suitable interface or protocol, such as the internet small computer system interface, among others. The network 1012 may be a cellular network, a radio network, a wide area network (WAN), a local area network (LAN), or the Internet, among others. An external comput- ing device may connect to the computer system 1000 through the network 1012. In some examples, an external computing device may be an external web server or a cloud computing node.

It is to be understood that the block diagram of FIG. 10 is not intended to indicate that the computer system 1000 is to include all of the components shown in FIG. 10. Rather, the computer system 1000 can include any appropriate fewer or additional components not illustrated in FIG. 10 (e.g., additional memory components, embedded controllers, modules, additional network interfaces, etc.). Further, the aspects described herein with respect to computer system 1000 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects.

Additional aspects of identifying characteristic surgical workflows in surgical video are described below with respect to an example dataset. Any of the aspects described herein below or above can be combined with any other aspects to identify variations in surgical approaches.

A fundamental step in the effort to analyze and standardize surgical practice is understanding the impact of surgical workflows on clinical outcome measures. A surgical workflow is the order of surgical phases in a single surgical case. Variations between cases can lead to an intractable number of workflows in a dataset, hence a method is proposed for extracting key workflows that characterize a dataset.

The following example includes a dataset that contains 366 laparoscopic Roux-en-Y gastric bypass cases, each segmented into surgical phases to obtain workflows. According to aspects, the Levenshtein distance is used in combination with spectral clustering to find groups of similar cases with the expectation that each cluster has its own characteristic workflows. The number of clusters is determined by the gap statistic with a reference model provided by a Markov chain. Sequential pattern mining combined with a uniqueness constraint is used to extract characteristic workflows for each cluster.

Aspects of the invention described herein identify characteristic workflows for each cluster in the dataset. These characteristic surgical workflows were assessed by a person with a medical background who is familiar with the procedure to describe the main clinical features. Aspects described herein provide a methodology that clusters cases according to their surgical workflow and enables these clusters to be interpreted clinically. Characteristic surgical workflows can be used to analyze the impact on surgical outcomes.

Roux-en-Y gastric bypass surgery is an example of a procedure that is highly variable in terms of delivery and outcomes. Identifying deviations in delivery can help to standardize behavior and reduce inefficiencies, for an improved quality of care globally.

A surgical procedure can be represented by surgical process models (SPMs) at varying levels of granularity and as described herein an SPM, called a workflow, includes an ordered sequence of surgical phases. The aim of one or more aspects of the present invention is to identify groups of similar workflows from a diverse dataset and extract characteristic workflows that define these groups. This can reduce the complexity of correlating surgical workflows with key success indicators such as patient outcome, and time and cost efficiencies.

The dataset used in the example includes 366 laparoscopic Roux-en-Y gastric bypass cases annotated with surgical phases covering the entire duration of the case without gaps. Spectral clustering, using the Levenshtein distance, is applied to cluster the workflows. The optimal number of clusters is chosen using the gap statistic. The existing formulation of the gap statistic cannot be applied directly to sequence data and as described herein, a Markov chain model is used to generate reference datasets for this purpose.

Continuing with the example, once the dataset has been partitioned into clusters, frequent sequential pattern (FSP) mining is used to extract frequent sequential patterns from the surgical workflows within each cluster. The resulting set of FSPs can be large and hard to interpret for highly variable datasets. Furthermore, a lot of the FSPs are short, occur in most of the workflows and are of little interest in defining features characteristic to a single cluster.

For this reason, in one or more aspects, a uniqueness score is defined to identify characteristic workflows for a cluster: uniqueness(FSPk,Ck)=support(FSPk,Ck)/support(FSPk,X), where FSPk is a frequent sequential pattern in cluster k, Ck is the set of workflows in cluster k and X is the full set of workflows. This score is 1 when FSPk only has support in its own cluster Ck, and 0 when it has no support. The unique FSPs, i.e., the characteristic workflows for a cluster, are therefore defined using a uniqueness threshold $u_{min}$.

In this example, the gap statistic selects the optimal number of clusters to be k=4. It should be noted that the gap function can rise again indicating the presence of nested subclusters which occurs for the data in this example when k=8.

Figure 13:
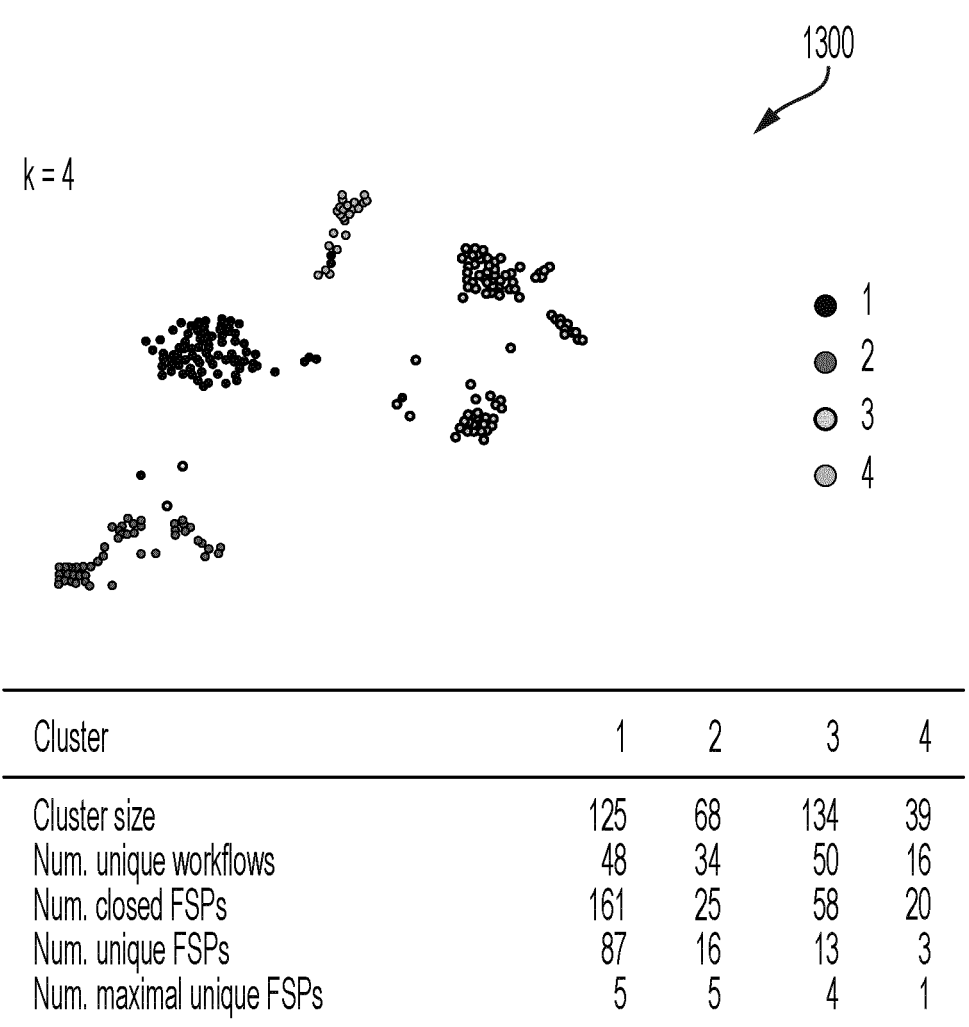
FIG. 13 depicts an example of a visualization when there are four clusters in accordance with one or more aspects.
Figure 14:
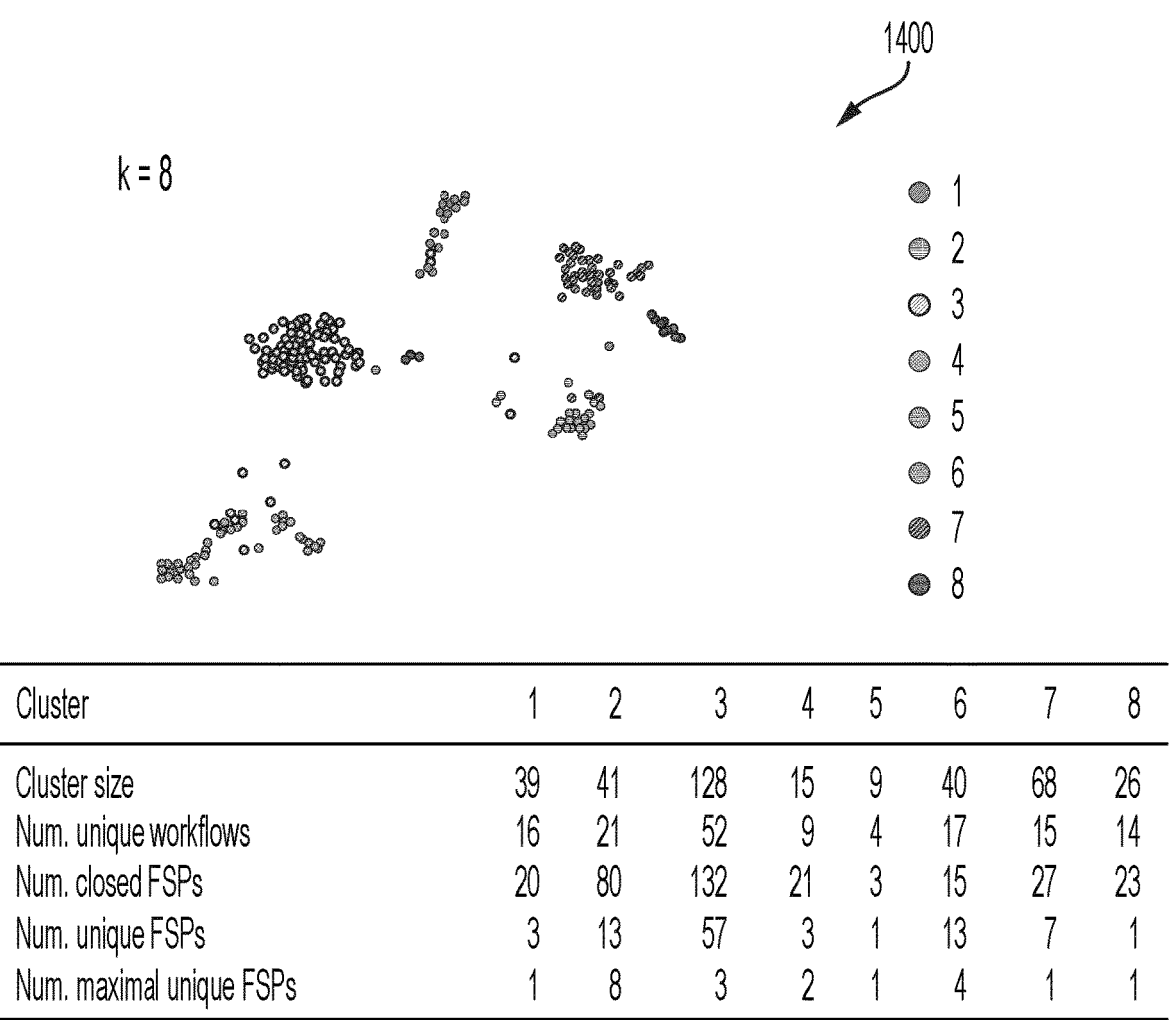
FIG. 14 depicts an example of a visualization when there are eight clusters in accordance with one or more aspects.

The properties of the clusters are summarized in FIG. 13 for k=4 and in FIG. 14 for k=8. FIG. 13 depicts an example of a visualization 1300 when there are four clusters in accordance with one or more aspect, and FIG. 14 depicts an example of a visualization 1400 when there are eight clusters in accordance with one or more aspects. The majority of the clusters in this example have a large number of closed FSPs and unique FSPs, however, filtering to the maximal unique FSPs results in a manageable number per cluster. The maximal unique FSPs for each cluster are shown in FIGS. 15 and 16 for k=4. In addition, the top 7 most frequently observed workflows in each cluster are displayed in FIGS. 15 and 16.

The following observations can be made about visualization 1500 of FIG. 15 and visualization 1600 of FIG. 16. The surgical approach observed in Cluster 1 and 4 proceeds through the patient anatomy from top to bottom. In this top-down approach, phases related to the stomach are performed first, followed by phases related to the intestines. In contrast, the approach in Cluster 2 proceeds from bottom to top through the patient anatomy. The workflows in Cluster 3 follow an approach that alternates between the stomach and the intestines. Another observation can be made by looking at Cluster 2. In some workflows two additional phases are seen: "Creation of Mesocolic Window" and "Retrieve Roux Limb." These two phases are associated with a retrocolic anastomosis approach, which was the dominant approach when the Rouxen-Y gastric bypass was first introduced.

One or more aspects described herein identify characteristic surgical workflows in a dataset of laparoscopic Roux-en-Y gastric bypass videos. A person familiar with the procedure was consulted to elucidate the characteristic patterns. The clusters were found to correspond to clinically different approaches to the Roux-en-Y gastric bypass, with each cluster containing minor variations of the main approach. A further investigation into nested subclusters was able to separate workflows into one cluster containing workflows following a retrocolic approach to the Roux-en-Y gastric bypass and other clusters containing workflows following an antecolic approach.

The ability to find clinically meaningful structure in a dataset of surgical workflows paves the way to studies linking workflows to patient outcomes and cost and efficiency measures. This, in turn, is fundamental for standardizing surgery and for discussions on best surgical practices.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
   a machine learning training system comprising one or more machine learning models that are trained to identify a plurality of surgical phases in a video of a surgical procedure; and
   a data analysis system configured to identify different surgical approaches in a plurality of videos capturing a same type of surgical procedure, wherein the identifying different surgical approaches comprises:
      receiving a plurality of surgical videos, each of the plurality of surgical videos capturing a workflow of the same type of surgical procedure;
      segmenting each of the plurality of surgical videos into a plurality of surgical phases based on surgical phases identified by the machine learning training system;
      generating a plurality of symbols representing each segment in each of the plurality of surgical videos to form symbolic representations of the plurality of surgical videos as workflows comprising ordered sequences of the surgical phases;
      clustering the symbolic representations of the plurality of surgical videos to form clusters of surgical videos having similar phase sequences; and
   outputting the clusters to a display device for display, wherein each of the clusters represents a different surgical approach for the same type of surgical procedure.

2. The system of claim 1, wherein the identifying different surgical approaches further comprises outputting an indication of a surgical service provider associated with one or more of the surgical videos or clusters to the display device for display.

3. The system of claim 2, wherein the surgical service provider is a group of physicians at a hospital.

4. The system of claim 2, wherein the surgical service provider is a physician.

5. The system of claim 2, wherein the identifying different surgical approaches further comprises outputting, to the display device, metrics related to surgical approaches taken by different surgical service providers.

6. The system of claim 1, wherein the clustering comprises:

calculating a distance metric between each pair of the plurality of surgical videos;

storing the calculated distance metrics in a distance matrix; and clustering similar workflows based at least in part on the distance matrix.

7. The system of claim 1, wherein the identifying different surgical approaches further comprises adding a label to each of the different surgical approaches and outputting the labels to the display device.

8. A computer-implemented method comprising:

receiving, by a processor, a plurality of surgical videos, each of the plurality of surgical videos capturing a workflow of a same type of surgical procedure;

segmenting each of the plurality of surgical videos into surgical phases;

generating a plurality of symbols representing each segment in each of the plurality of surgical videos to form symbolic representations of the plurality of surgical videos as workflows comprising ordered sequences of the surgical phases;

clustering, by the processor, the plurality of surgical videos into clusters of similar workflows, the clustering based at least in part on the ordered sequences of the surgical phases of each of the surgical videos; and identifying, by the processor, surgical approaches that are unique to each of the clusters, the identifying based at least in part on the surgical phases of each of the surgical videos.

9. The computer-implemented method of claim 8, further comprising labeling each of the unique surgical approaches.

10. The computer-implemented method of claim 8, wherein the applying clustering techniques comprises:

calculating a distance metric between each pair of the plurality of surgical videos;

storing the calculated distance metrics in a distance matrix; and clustering similar workflows based at least in part on the distance matrix.

11. The computer-implemented method of claim 10, further comprising determining optimal clustering hyperparameters for the plurality of surgical videos.

12. The computer-implemented method of claim 8, further comprising outputting, by the processor to a display device, a graphical representation of the workflows in the clusters of similar workflows and the identified surgical approaches.

13. The computer-implemented method of claim 12, wherein the graphical representation identifies a surgical service provider associated with each of the workflows.

14. A computer program product comprising a memory device having computer-executable instructions stored thereon, which when executed by one or more processors cause the one or more processors to perform operations comprising:

visualizing different surgical approaches used by service providers when performing a surgical procedure, the visualizing comprising:

receiving a plurality of surgical videos, each of the plurality of surgical videos capturing a workflow of a service provider performing the surgical procedure;

segmenting each of the plurality of surgical videos into surgical phases;

generating a plurality of symbols representing each segment in each of the plurality of surgical videos to form symbolic representations of the plurality of surgical videos as workflows comprising ordered sequences of the surgical phases;

clustering the plurality of surgical videos into clusters of similar workflows, the clustering based at least in part on the ordered sequences of the surgical phases of each of the surgical videos;

identifying surgical approaches that are unique to each of the clusters, the identifying based at least in part on the surgical phases of each of the surgical videos; and outputting, to a display device, a graphical representation of the identified surgical approaches.

15. The computer program product of claim 14, wherein the visualizing further comprises:

receiving user input via a user interface of the graphical representation; and in response to the user input, outputting to the display device, a second graphical representation that includes providers that use the identified surgical approaches.

16. The computer program product of claim 14, wherein the visualizing further comprises:

receiving user input via a user interface of the graphical representation; and in response to the user input, outputting to the display device, a second graphical representation that includes a label describing each of the identified surgical approaches.

17. The computer program product of claim 14, wherein the visualizing further comprises:

receiving user input via a user interface of the graphical representation; and in response to the user input, outputting to the display device, a second graphical representation that includes additional information describing characteristics of one or both of a service provider or a patient.

18. The computer program product of claim 14, wherein the clustering comprises:

calculating a distance metric between each pair of the plurality of surgical videos;

storing the calculated distance metrics in a distance matrix; and clustering similar workflows based at least in part on the distance matrix.

* * * * *